(12) United States Patent
Huber et al.

(10) Patent No.: US 8,254,368 B2
(45) Date of Patent: Aug. 28, 2012

(54) FEMTOCELL ARCHITECTURE FOR INFORMATION MANAGEMENT

(75) Inventors: Kurt Donald Huber, Coral Springs, FL (US); William Gordon Mansfield, Sugar Hill, GA (US); Judson John Flynn, Decatur, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 501 days.

(21) Appl. No.: 12/465,468

(22) Filed: May 13, 2009

(65) Prior Publication Data
US 2009/0286540 A1 Nov. 19, 2009

Related U.S. Application Data

(60) Provisional application No. 61/052,813, filed on May 13, 2008.

(51) Int. Cl.
*H04J 3/06* (2006.01)
(52) U.S. Cl. ........ 370/350; 370/310; 370/328; 370/338; 370/342; 455/436; 455/442; 455/445
(58) Field of Classification Search .................. None
See application file for complete search history.

(56) References Cited

U.S. PATENT DOCUMENTS

| | | | |
|---|---|---|---|
| 5,745,559 A | 4/1998 | Weir | |
| 5,864,764 A | 1/1999 | Thro et al. | |
| 6,052,594 A | 4/2000 | Chuang et al. | |
| 6,151,505 A | 11/2000 | Larkins | |
| 6,219,786 B1 | 4/2001 | Cunningham et al. | |
| 6,266,537 B1 | 7/2001 | Kashitani et al. | |
| 6,363,261 B1 | 3/2002 | Raghavan | |
| 6,483,852 B1 | 11/2002 | Jacquet et al. | |
| 6,484,096 B2 | 11/2002 | Wong | |
| 6,710,651 B2 | 3/2004 | Forrester | |
| 6,718,023 B1 | 4/2004 | Zolotov | |
| 7,080,139 B1 | 7/2006 | Briggs et al. | |
| 7,142,861 B2 | 11/2006 | Murai | |
| 7,146,153 B2 | 12/2006 | Russell | |
| 7,209,739 B1 | 4/2007 | Narayanabhatla | |

(Continued)

FOREIGN PATENT DOCUMENTS
GB 2425921 A 11/2006

OTHER PUBLICATIONS

International Search Report and Written Opinion dated Oct. 27, 2009 for PCT Application No. PCT/US2009/043861, 14 Pages.

(Continued)

*Primary Examiner* — Hassan Phillips
*Assistant Examiner* — Gautam Sharma
(74) *Attorney, Agent, or Firm* — Turocy & Watson, LLP

(57) ABSTRACT

A system and methodology that significantly reduces traffic in a backhaul pipe of a femto access point (AP) and organizes content delivery is provided. Specifically, an aggregator/routing platform is employed to connect multiple femto APs in a femto enterprise to a single backhaul network. The aggregator/routing platform collects and analyzes information from the multiple femtos and directly route communication packets to between femto APs within the enterprise when possible, without employing the backhaul network. Content and/or tasks can be internally organized between devices connected to the multiple femtos, without accessing the core network. During internal communication, a control link can preserved and sent to the core network to facilitate billing.

20 Claims, 17 Drawing Sheets

U.S. PATENT DOCUMENTS

| | | | |
|---|---|---|---|
| 7,277,410 B2 | 10/2007 | Horneman | |
| 7,317,931 B2 | 1/2008 | Guo | |
| 7,370,356 B1 | 5/2008 | Guo | |
| 7,496,383 B2 | 2/2009 | Kurata | |
| 7,516,219 B2 | 4/2009 | Moghaddam et al. | |
| 7,613,444 B2 | 11/2009 | Lindqvist et al. | |
| 7,623,857 B1 | 11/2009 | O'Neil et al. | |
| 7,633,910 B2 | 12/2009 | Zhun et al. | |
| 7,751,826 B2 | 7/2010 | Gardner | |
| 7,761,526 B2 | 7/2010 | Pounds et al. | |
| 7,768,983 B2 | 8/2010 | Nylander et al. | |
| 7,885,644 B2 | 2/2011 | Gallagher et al. | |
| 7,929,537 B2 | 4/2011 | Vasudevan et al. | |
| 7,929,970 B1 | 4/2011 | Gunasekara | |
| 7,941,144 B2 | 5/2011 | Nylander et al. | |
| 7,995,994 B2 | 8/2011 | Khetawat et al. | |
| 8,108,923 B1 | 1/2012 | Satish et al. | |
| 2002/0098837 A1 | 7/2002 | Ferrario et al. | |
| 2002/0123365 A1 | 9/2002 | Thorson | |
| 2002/0142791 A1 | 10/2002 | Chen et al. | |
| 2003/0109271 A1 | 6/2003 | Lewis et al. | |
| 2003/0125044 A1 | 7/2003 | Deloach | |
| 2003/0142637 A1 | 7/2003 | Khawer et al. | |
| 2003/0153302 A1 | 8/2003 | Lewis et al. | |
| 2004/0111382 A1 | 6/2004 | Haji-Ioannou | |
| 2004/0125781 A1 | 7/2004 | Walter et al. | |
| 2004/0236702 A1 | 11/2004 | Fink et al. | |
| 2004/0258003 A1 | 12/2004 | Kotot et al. | |
| 2005/0003797 A1 | 1/2005 | Baldwin | |
| 2005/0009499 A1 | 1/2005 | Koster | |
| 2005/0026650 A1* | 2/2005 | Russell | 455/554.1 |
| 2005/0075114 A1 | 4/2005 | Dennison et al. | |
| 2005/0108529 A1 | 5/2005 | Juneau | |
| 2005/0144279 A1 | 6/2005 | Wexelblat | |
| 2005/0160276 A1 | 7/2005 | Braun et al. | |
| 2005/0172148 A1 | 8/2005 | Ying | |
| 2005/0177645 A1 | 8/2005 | Dowling et al. | |
| 2005/0223389 A1 | 10/2005 | Klein et al. | |
| 2005/0250527 A1 | 11/2005 | Jugl | |
| 2005/0254451 A1 | 11/2005 | Grosbach | |
| 2005/0269402 A1 | 12/2005 | Spitzer et al. | |
| 2006/0031387 A1 | 2/2006 | Hamzeh et al. | |
| 2006/0031493 A1 | 2/2006 | Cugi | |
| 2006/0046647 A1 | 3/2006 | Parikh et al. | |
| 2006/0075098 A1 | 4/2006 | Becker et al. | |
| 2006/0182074 A1 | 8/2006 | Kubler et al. | |
| 2006/0223498 A1 | 10/2006 | Gallagher et al. | |
| 2006/0281457 A1 | 12/2006 | Huotari et al. | |
| 2007/0002844 A1 | 1/2007 | Ali | |
| 2007/0008894 A1 | 1/2007 | Lynch et al. | |
| 2007/0025245 A1 | 2/2007 | Porras et al. | |
| 2007/0032225 A1 | 2/2007 | Konicek et al. | |
| 2007/0032269 A1 | 2/2007 | Shostak | |
| 2007/0074272 A1 | 3/2007 | Watanabe | |
| 2007/0097938 A1* | 5/2007 | Nylander et al. | 370/338 |
| 2007/0097939 A1 | 5/2007 | Nylander et al. | |
| 2007/0097983 A1 | 5/2007 | Nylander et al. | |
| 2007/0099561 A1 | 5/2007 | Voss | |
| 2007/0124802 A1 | 5/2007 | Anton et al. | |
| 2007/0155421 A1 | 7/2007 | Alberth et al. | |
| 2007/0167175 A1 | 7/2007 | Wong | |
| 2007/0183427 A1 | 8/2007 | Nylander et al. | |
| 2007/0184815 A1* | 8/2007 | Aebi | 455/406 |
| 2007/0199076 A1 | 8/2007 | Rensin et al. | |
| 2007/0258418 A1 | 11/2007 | Wurtenberger et al. | |
| 2007/0270152 A1 | 11/2007 | Nylander et al. | |
| 2007/0275739 A1 | 11/2007 | Blackburn | |
| 2007/0287501 A1 | 12/2007 | Hoshina | |
| 2008/0043972 A1 | 2/2008 | Ruetschi et al. | |
| 2008/0049702 A1 | 2/2008 | Meylan et al. | |
| 2008/0065752 A1 | 3/2008 | Ch'ng et al. | |
| 2008/0076392 A1* | 3/2008 | Khetawat et al. | 455/411 |
| 2008/0076393 A1 | 3/2008 | Khetawat et al. | |
| 2008/0076398 A1 | 3/2008 | Mate et al. | |
| 2008/0076412 A1 | 3/2008 | Khetawat et al. | |
| 2008/0076419 A1 | 3/2008 | Khetawat et al. | |
| 2008/0076420 A1 | 3/2008 | Khetawat et al. | |
| 2008/0076425 A1 | 3/2008 | Khetawat et al. | |
| 2008/0081636 A1 | 4/2008 | Nylander et al. | |
| 2008/0082538 A1 | 4/2008 | Meijer et al. | |
| 2008/0126531 A1 | 5/2008 | Setia et al. | |
| 2008/0132239 A1 | 6/2008 | Khetawat et al. | |
| 2008/0133742 A1 | 6/2008 | Southiere et al. | |
| 2008/0151807 A1* | 6/2008 | Meier et al. | 370/312 |
| 2008/0168099 A1 | 7/2008 | Skaf | |
| 2008/0181184 A1 | 7/2008 | Kezys | |
| 2008/0207170 A1 | 8/2008 | Khetawat et al. | |
| 2008/0242280 A1 | 10/2008 | Shapiro et al. | |
| 2008/0244148 A1 | 10/2008 | Nix et al. | |
| 2008/0254792 A1 | 10/2008 | Ch'ng | |
| 2008/0261602 A1* | 10/2008 | Livneh | 455/442 |
| 2008/0281687 A1 | 11/2008 | Hurwitz et al. | |
| 2008/0282327 A1 | 11/2008 | Winget et al. | |
| 2008/0299984 A1 | 12/2008 | Shimomura | |
| 2008/0299992 A1 | 12/2008 | Eitan et al. | |
| 2008/0305792 A1 | 12/2008 | Khetawat et al. | |
| 2008/0305801 A1 | 12/2008 | Burgess et al. | |
| 2008/0318551 A1 | 12/2008 | Palamara et al. | |
| 2009/0012898 A1 | 1/2009 | Sharma et al. | |
| 2009/0037973 A1 | 2/2009 | Gustave et al. | |
| 2009/0042593 A1 | 2/2009 | Yavuz et al. | |
| 2009/0046665 A1 | 2/2009 | Robson et al. | |
| 2009/0047945 A1 | 2/2009 | Zhang | |
| 2009/0061821 A1 | 3/2009 | Chen et al. | |
| 2009/0061873 A1 | 3/2009 | Bao et al. | |
| 2009/0082010 A1 | 3/2009 | Lee | |
| 2009/0082020 A1 | 3/2009 | Ch'ng et al. | |
| 2009/0092096 A1 | 4/2009 | Czaja | |
| 2009/0092097 A1 | 4/2009 | Nylander et al. | |
| 2009/0093232 A1 | 4/2009 | Gupta et al. | |
| 2009/0094351 A1 | 4/2009 | Gupta et al. | |
| 2009/0094680 A1 | 4/2009 | Gupta et al. | |
| 2009/0097436 A1 | 4/2009 | Vasudevan et al. | |
| 2009/0111499 A1 | 4/2009 | Bosch | |
| 2009/0122773 A1 | 5/2009 | Gogic | |
| 2009/0124262 A1 | 5/2009 | Vela et al. | |
| 2009/0131050 A1 | 5/2009 | Osborn | |
| 2009/0135749 A1 | 5/2009 | Yang | |
| 2009/0135794 A1 | 5/2009 | Su et al. | |
| 2009/0156213 A1 | 6/2009 | Spinelli et al. | |
| 2009/0163216 A1 | 6/2009 | Hoang et al. | |
| 2009/0163224 A1 | 6/2009 | Dean | |
| 2009/0164547 A1 | 6/2009 | Ch'ng et al. | |
| 2009/0170440 A1 | 7/2009 | Eyuboglu et al. | |
| 2009/0170528 A1 | 7/2009 | Bull et al. | |
| 2009/0180893 A1* | 7/2009 | Viswanath | 370/328 |
| 2009/0191844 A1 | 7/2009 | Morgan et al. | |
| 2009/0191845 A1 | 7/2009 | Morgan et al. | |
| 2009/0210324 A1 | 8/2009 | Bhogal | |
| 2009/0213825 A1* | 8/2009 | Gupta et al. | 370/338 |
| 2009/0215452 A1 | 8/2009 | Balasubramanian et al. | |
| 2009/0221303 A1 | 9/2009 | Soliman | |
| 2009/0233574 A1 | 9/2009 | Shinozaki | |
| 2009/0245176 A1 | 10/2009 | Balasubramanian et al. | |
| 2009/0253421 A1 | 10/2009 | Camp et al. | |
| 2009/0253432 A1 | 10/2009 | Willey et al. | |
| 2009/0279701 A1 | 11/2009 | Moisand et al. | |
| 2009/0291667 A1 | 11/2009 | Vakil et al. | |
| 2010/0022266 A1 | 1/2010 | Villier | |
| 2010/0040026 A1 | 2/2010 | Melkesetian | |
| 2010/0260068 A1 | 10/2010 | Bhatt et al. | |
| 2011/0200022 A1 | 8/2011 | Annamalai | |

OTHER PUBLICATIONS

OA dated Aug. 18, 2011 for U.S. Appl. No. 12/275,416, 39 pages.
OA dated Sep. 14, 2011 for U.S. Appl. No. 12/276,002, 35 pages.
OA dated Oct. 5, 2011 for U.S. Appl. No. 12/276,058, 37 pages.
OA dated Oct. 6, 2011 for U.S. Appl. No. 12/465,483, 50 pages.
OA dated Oct. 4, 2011 for U.S. Appl. No. 12/484,135, 44 pages.
OA dated Jul. 21, 2011 for U.S. Appl. No. 12/175,293, 30 pages.
OA dated Mar. 29, 2011 for U.S. Appl. No. 12/276,002, 37 pages.
OA dated Apr. 13, 2011 for U.S. Appl. No. 12/276,058, 40 pages.
OA dated Apr. 19, 2011 for U.S. Appl. No. 12/276,238, 22 pages.
OA dated May 5, 2011 for U.S. Appl. No. 12/275,015, 32 pages.
OA dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog1569; © 2009 Allied Business Intelligence, Inc.
OA dated Jun. 14, 2011 for U.S. Appl. No. 12/275,878, 35 pages.
OA dated Jun. 22, 2011 for U.S. Appl. No. 12/484,072, 38 pages.
OA dated Jul. 7, 2011 for U.S. Appl. No. 12/276,257, 24 pages.
OA dated Jun. 28, 2011 for U.S. Appl. No. 12/275,925, 18 pages.
OA dated Jun. 8, 2011 for U.S. Appl. No. 12/484,026, 30 pages.
International Search Report and Written Opinion mailed Feb. 23, 2010, for PCT Application No. PCT/US2009/043846, 13 pages.
OA dated Dec. 31, 2009 for U.S. Appl. No. 11/457,129, 16 pages.
OA dated Apr. 17, 2009 for U.S. Appl. No. 11/276,269, 15 pages.
OA dated Nov. 4, 2008 for U.S. Appl. No. 11/276,269, 15 pages.
OA dated Oct. 24, 2011 for U.S. Appl. No. 12/275,925, 14 pages.
OA dated Nov. 30, 2011 for U.S. Appl. No. 12/275,878, 38 pages.
OA dated Dec. 1, 2011 for U.S. Appl. No. 12/275,996, 44 pages.
OA dated Oct. 25, 2011 for U.S. Appl. No. 12/465,580, 39 pages.
OA dated Jan. 5, 2012 for U.S. Appl. No. 12/465,585, 43 pages.
OA dated Dec. 28, 2011 for U.S. Appl. No. 12/175,293, 38 pages.
OA dated Nov. 21, 2011 for U.S. Appl. No. 12/484,026, 37 pages.
OA dated Dec. 14, 2011 for U.S. Appl. No. 12/484,072, 44 pages.
OA dated Nov. 1, 2011 for U.S. Appl. No. 12/816,087, 33 pages.
OA dated Mar. 5, 2012 for U.S. Appl. No. 12/465,598, 55 pages.
OA dated Mar. 19, 2012 for U.S. Appl. No. 12/276,120, 68 pages.
OA dated Mar. 30, 2012 for U.S. Appl. No. 12/484,026, 30 pages.
Notice of Allowance dated Apr. 3, 2012 for U.S. Appl. No. 12/275,996, 38 pages.
OA dated Apr. 10, 2012 for U.S. Appl. No. 12/275,416, 32 pages.
OA dated Apr. 10, 2012 for U.S. Appl. No. 12/484,135, 45 pages.
OA dated Apr. 13, 2012 for U.S. Appl. No. 13/316,106, 35 pages.
OA dated May 8, 2012 for U.S. Appl. No. 11/457,129, 38 pages.

* cited by examiner

FEMTOCELL ARCHITECTURE FOR INFORMATION MANAGEMENT

CROSS-REFERENCE TO RELATED APPLICATIONS

This application claims the benefit of U.S. Provisional Patent Application Ser. No. 61/052,813, filed on May 13, 2008, entitled "Management of access of Femto Cell Coverage." This application is also related to co-pending U.S. patent application Ser. No. 12/465,483, filed on May 13, 2009, entitled "Location-based Services in a Femtocell network", co-pending U.S. patent application Ser. No. 12/465,580, filed on May 13, 2009, entitled "Commerce and Services in a Femtocell Network", and co-pending U.S. patent application Ser. No. 12/465,585, filed on May 13, 2009, entitled "Intra-premises Content Management in a Femtocell Network". The entireties of which are incorporated herein by reference.

TECHNICAL FIELD

The subject innovation relates to wireless communications and, more particularly, employing a femto cell enterprise architecture that facilitates content and/or task organization.

BACKGROUND

Femto cells—building-based wireless access points interfaced with a wired broadband network—are generally deployed to improve indoor wireless coverage and to offload a mobility radio access network (RAN) operated by a wireless network and service provider. Femto cells typically operate in licensed portions of the electromagnetic spectrum, and generally offer plug-and-play installation; e.g., automatic configuration of femto access point. Improved indoor coverage includes stronger signal and improved reception (e.g., voice or data), ease of session or call initiation, and session or call retention as well. Offloading a RAN reduces operational and transport costs for a service provider since a lesser number of end users utilizes over-the-air (OTA) radio resources (e.g., radio frequency bands and channels), which are typically limited.

Coverage of a femto cell, or femto access point (AP), is generally intended to be confined within the bounds of an indoor compound (e.g., a residential or commercial building) in order to mitigate interference among mobile stations covered by a macro cell and terminals covered by the femto AP. Additionally, confined coverage can reduce cross-talk among terminals serviced by disparate, neighboring femto cells as well. Femto cells typically operate in licensed portions of the electromagnetic spectrum, and generally offer plug-and-play installation; e.g., automatic configuration of femto AP subsequent to femto cell subscriber registration with a service provider. Coverage improvements via femto cells can also mitigate customer attrition as long as a favorable subscriber perception regarding voice coverage and other data services with substantive delay sensitivity, or otherwise, is attained. In addition, a richer variety of wireless voice and data services can be offered to customers via a femto cell since such service offerings do not rely primarily on mobility RAN resources.

With an increase in the number of devices attached to a femto cell, the traffic on the backhaul network of the femto cell can increase significantly. This can cause congestion in the backhaul network and delays during communication, which can lead to end user frustration.

SUMMARY

The following presents a simplified summary of the specification in order to provide a basic understanding of some aspects of the specification. This summary is not an extensive overview of the specification. It is intended to neither identify key or critical elements of the specification nor delineate the scope of the specification. Its sole purpose is to present some concepts of the specification in a simplified form as a prelude to the more detailed description that is presented later.

The systems and methods disclosed herein, in one aspect thereof, can facilitate reduction in backhaul network traffic and communication delay by employing an enterprise femto architecture. The enterprise femto architecture employs a routing platform to connect multiple femtos access points to a common femto gateway to generate a mesh network. In particular, the routing platform can be employed to facilitate internal communication between devices attached to disparate femto access points in the mesh network and facilitate external communications to the core network by routing communication packets from a femto access point in the mesh network to a backhaul network. Additionally, routing of the packets at the routing platform can be monitored and a billing database can be updated based in part on the routing.

According to an aspect of the system, a content/task organization component can be employed to organize content and or tasks within the femto enterprise. Moreover, the content/task organization component can facilitate transfer of content and/or information associated with tasks within the femto architecture, such that, the core network is not accessed. Further, the content/task organization component can facilitate automatic synchronization of information in devices attached to different femtos in the enterprise network without accessing core network and thus reducing traffic on the backhaul network. Contact lists, calendar events, task lists, etc. on devices attached to multiple femto APs in the femto enterprise can be synchronized, updated and/or organized by the content/task organization component. Furthermore, the content/task organization component can transfer content that is purchased and/or downloaded from the core network to multiple devices attached to a femto in the femto enterprise network, without each device accessing the core network.

In accordance with another aspect of the system, a route determination component can analyze the received packet to facilitate routing of the packet from the routing platform. Moreover, the route determination component can determine a destination address, source address, type of packet, type of protocol associated with the packet, and/or one or more user defined rules or policies and/or user preferences, etc. Based in part on the determined information, the route determination component can compute an optimal route to transfer the received packet, such that, backhaul network bandwidth is efficiently utilized. In one example, the route determination component can determine an optimal route for a received packet by employing load-balancing techniques, to avoid network congestion in the backhaul pipe. Additionally or alternately, the route determination component can employ one or more machine learning techniques to facilitate efficient network and/or resource utilization. Further, the route determination component can also perform a cost-benefit analysis to determine an optimal route associated with minimal billing charges.

Yet another aspect of the disclosed subject matter relates to a method that employs a femto enterprise architecture to improve network performance and response times. The method comprises receiving a packet at a routing platform, from a UE attached to a femto within the enterprise femto architecture. Further, an analysis is performed on the received packet to determine information associated with routing of the packet (e.g. source address, destination address, etc.). Furthermore, a route can be determined for transferring the packet from the routing platform based in part on the analysis and/or user defined rules or policies and/or user preferences. If determined that the packet can be internally routed within the enterprise femto, a soft handover is performed and the packet is routed to the destination UE via a femto access point within the femto enterprise. In addition, control data associated with the communication is sent to the core network, to facilitate billing. According to an aspect, if determined that the packet cannot be internally routed within the enterprise femto, a hard handover is performed the packet is routed to its destination over the core network via a backhaul pipe. In still another aspect, a method that can facilitate automatic synchronization of information in devices attached to different femtos in the enterprise network without accessing core network is provided. It can be appreciated that synchronization of information can be driven at least in part through access privileges determined via access list(s) such as white lists. Further, the method comprises distributing or transferring content, which is purchased and/or downloaded from the core network to multiple devices attached to a femto in the femto enterprise network, without each device accessing the core network.

Aspects, features, or advantages of the subject innovation can be exploited in substantially any wireless communication technology; e.g., Wi-Fi, Worldwide Interoperability for Microwave Access (WiMAX), Enhanced General Packet Radio Service (Enhanced GPRS), Third Generation Partnership Project (3GPP) Long Term Evolution (LTE), Third Generation Partnership Project 2 (3GPP2) Ultra Mobile Broadband (UMB), High Speed Packet Access (HSPA), or Zigbee. Additionally, substantially all aspects of the subject innovation can be exploited in legacy telecommunication technologies.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

DETAILED DESCRIPTION

Figure 1:
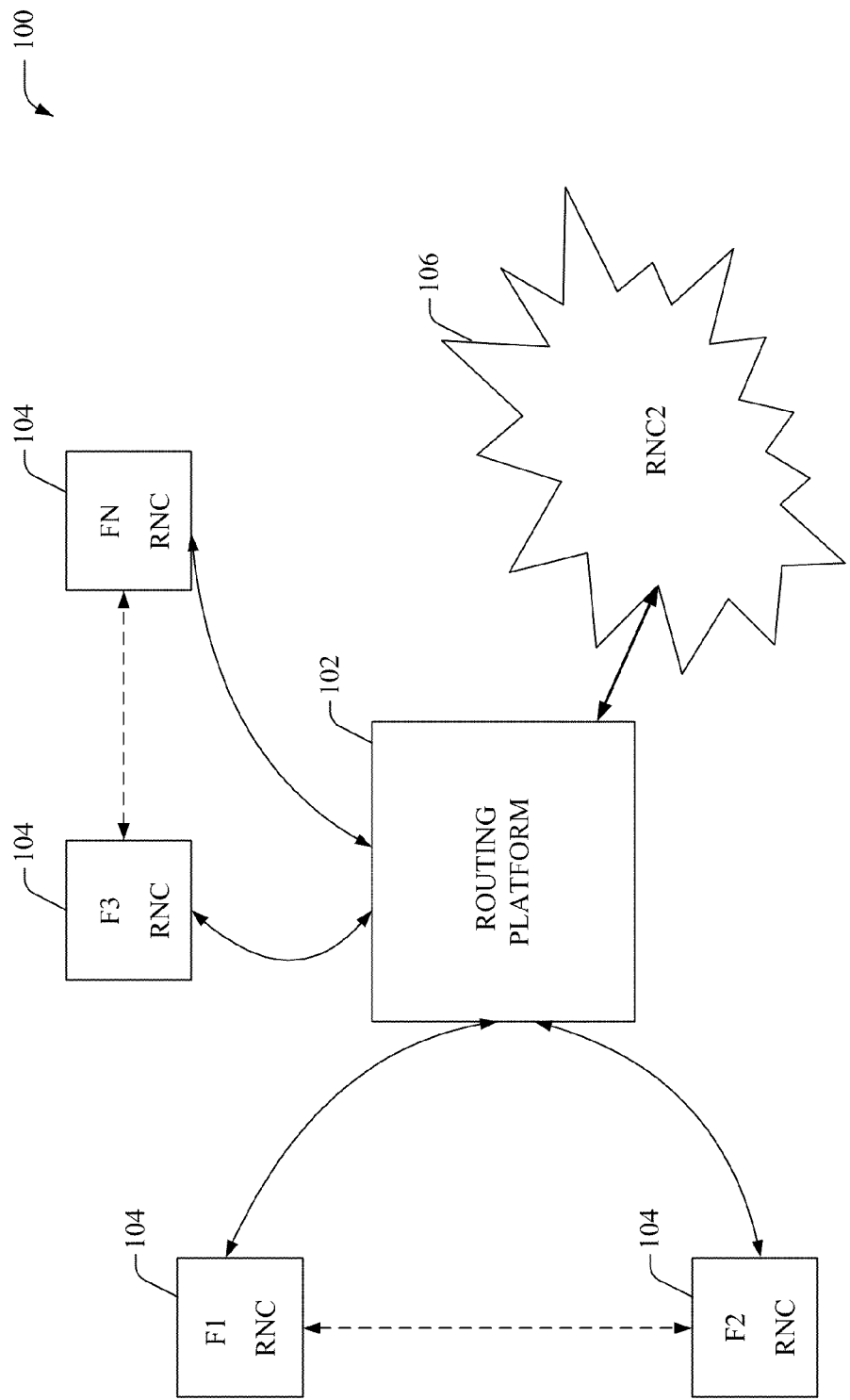
FIG. 1 illustrates an example high-level system diagram depicting an enterprise femto architecture, according to an aspect of the subject specification.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, well-known structures and devices are shown in block diagram form in order to facilitate describing the claimed subject matter.

As used in this application, the terms "component," "module," "system," "interface," "platform," "service," "framework," "connector," or the like are generally intended to refer to a computer-related entity, either hardware, a combination of hardware and software, software, or software in execution or an entity related to an operational machine with one or more specific functionalities. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. As another example, an interface can include I/O components as well as associated processor, application, and/or API components.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms like "user equipment," "mobile station," "mobile," "subscriber station," "access terminal," "terminal," "handset," "appliance," "machine", and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B." "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "user," "subscriber," "customer," "consumer," "prosumer," "agent,", "owner" and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms) which can provide simulated vision, sound recognition and so forth. As utilized herein, the term "prosumer" indicate the following contractions: professional-consumer and producer-consumer. In addition, the terms "wireless network" and "network" are used interchangeable in the subject application, when context wherein the term is utilized warrants distinction for clarity purposes such distinction is made explicit. Likewise, the terms "femto cell access point", "femto access point", "femto" and the like are also utilized interchangeably.

Traditional approaches employ femto cells to improve wireless coverage, for example, in an enclosed area and/or to reduce traffic in the core network. User equipment (UE) within the femto coverage area typically communicates with the core network via the femto access point (AP). Typically, the UE can register with the femto AP and communication (voice and/or data traffic) can be routed to the subscriber through the femto AP. The femto AP employs a backhaul broadband wired network backbone to page/route packet communication (e.g., voice and data traffic, and signaling) to the core network. With an increase in the number of UEs connected to the femto AP, the traffic on the backhaul network is significantly increased.

Systems and/or methods are presented herein that provide an enterprise femto architecture to substantially reduce traffic in the backhaul network and organize content delivery. In one aspect, the enterprise femto architecture enables multiple femto APs to be connected to each other in a mesh structure. Further, a central aggregator/routing platform can be employed between the femto APs and the femto gateway, such that a single backhaul network can be employed for multiple femtos connected to the aggregator/routing platform. The aggregator/routing platform can collect information from the multiple femtos and further directly route communication internally within the enterprise when possible, without employing the backhaul network. Thus, the routing can reduce delays and traffic in the backhaul network.

The systems and methods disclosed herein employ an aggregator/routing platform that can determine routing information associated with a communication packet and accordingly route the packet, either internally within the enterprise, or externally to the core network via the backhaul pipe. In one aspect, a billing scheme is employed that can employ different rates based in part on the route employed. Further, content and task management and/or organization can be facilitated within the femto enterprise without accessing the core network.

Referring initially to FIG. 1, there illustrated is an example high-level system diagram 100 depicting an enterprise femto architecture, according to an aspect of the subject specification. Typically, a routing platform 102 can be employed to connect multiple femtos 104 to a femto gateway (not shown). Specifically, each femto 104 can include an RNC (radio network controller) and the routing platform 102 can be employed to connect the RNC of a femto 104 to disparate femtos 104 on the network as well as to an RNC2 106 of a femto gateway. It can be appreciated that, although RNCs are depicted in the figure to control Node Bs in the UMTS (Universal Mobile Telecommunications System) radio access network (UTRAN), most any controller can be employed for a disparate technology or network.

In one aspect, the routing platform 102 can be connected between multiple femtos 104, such that, the routing platform 102 can run Iur between the enterprise femtos 104 to enable soft handover in the enterprise femto environment 100. For example, the routing platform 102 can run voice between two femtos 104 or transfer content between two or more femtos 104. In one example, a femto enterprise architecture can be employed in a building, such as, but not limited to, a hotel, an office, hospital, a residential complex, a factory, a warehouse etc. Moreover, the routing platform 102 can facilitate communications between devices connected on disparate femtos without transferring the communication packets to the core network and thus reduce delays. According to an embodiment, the routing platform 102 can receive a communication packet from one of the multiple femtos 104 and can determine routing information associated with the packet. In one example, when the routing information indicates that the packet can be routed within the enterprise, the routing platform 102 can directly route the packet to a disparate femto in the enterprise femto without transferring the packet to the core network (e.g. via the femto gateway). As an example, consider a building scenario employing the enterprise femto architecture, wherein multiple femtos 104 can be deployed on each floor of the building. The femtos 104 can further be connected to a single backhaul pipe via the routing platform 102. In this example, a UE on the first floor, connected to the femto (e.g. femto F1) on the first floor can establish communication (e.g. voice, data, etc.) with another UE on the third floor connected to a femto (e.g. femto F3) on the third floor, without accessing the core network. Moreover, the routing platform 102 can be employed to directly connect the user planes and establish communication between the two femtos 104.

According to an embodiment, during internal communication within the enterprise, the routing platform 102 can preserve a control link for the femto gateway that can be employed by the core network to facilitate a billing process. The control link can be sent to the core network to update a billing database that can, for example, apply different charges for internal communication within the enterprise femto and external communication with the core network. Typically, charges associated with internal communication can be lower than those associated with external communication. In one aspect, the control link can also be stored in a database (not shown) connected to the routing platform 102, for example a buffer, such that, if a failure occurs in the core network, internal communication within the enterprise can continue uninterruptedly. The saved control data can be transferred to the core network for billing purposes when the core network is operational.

In accordance with another embodiment, the enterprise femto structure can facilitate multiple billing schemes associated with the wireless service provider. In one example scheme, the wireless service provider can charge a fixed rate for external communication, for example, when the packet received at the routing platform 102 is routed to the core network via the backhaul pipe, and internal communication within the mesh network can be free of charge. However, in this scheme the service provider can charge a fee for most any maintenance associated with the mesh network. According to another example billing scheme, the wireless service provider can provide maintenance of the mesh network free of cost, but can charge a high rate for external communication with the core network and a lower rate for internal communication within the mesh network. It can be appreciated that the subject specification is not limited to the aforementioned billing scheme and most any billing scheme can be employed. Moreover, the charges can be predefined by a wireless service provider and/or operator. In addition, the charges can also be dynamically modified based on available network bandwidth.

FIG. 1 illustrates four femtos 104 connected to the routing platform 102, however it can be appreciated that N femtos can be connected to the routing platform 102, wherein N can be a natural number from 1 to infinity. Moreover, the number of femtos 104 connected to the routing platform 102 can be based in part on a number of ports and/or bandwidth available on the routing platform 102. According to one embodiment of the enterprise femto architecture, multiple femtos 104 can be connected to a single routing platform 102 and further, multiple routing platforms (not shown) can be connected together to create a larger mesh structure. For example, one routing platform can be deployed on each floor of a building (e.g. an office) and the routing platforms on each floor can be connected together to create an enterprise femto mesh structure that can cover the entire building. The multiple routing platforms can communicate with each other such that each routing platform knows the femtos associated with each routing platform and devices currently connected to the femtos, which can facilitate internal routing.

Referring back to FIG. 1, the routing platform 102 can receive routing information associated with most any communication packet from a femto 104 connected to the routing platform 102. In one aspect, the routing information can indicate that the packet has to be transferred to the core network. Accordingly, the routing platform 102 can perform a hard handover and direct the packet to the core network via the femto gateway. In another aspect, the routing information can indicate that the packet can be transferred internally to another femto 104 connected to the routing platform 102. Moreover, in this case, the routing platform 102 can perform a soft handover between the femtos and establish communication, such that, dead spots and/or issue scenarios can be avoided. Further, the routing platform 102 can determine control information for traffic routed directly between femtos and route the control information to the core network via the backhaul pipe.

Each femto 104 connected to the routing platform 102 can have RNC functionality built into it. In particular, the routing platform 102 can be employed to connect the RNCs between the two femtos. Specifically, an Iur can be built that can be routed in the packet stream between the femtos. In one aspect, the built in RNC functionality can be employed to improve scalability. For example, if a femto needs to be added to the mesh, its RNC functionality can also be provided along with it and thus the mesh can be easily scaled. However, it can be appreciated that the backhaul pipe & control interface does not grow with an increase in the number of femtos 104 connected to the routing platform 102.

According to one aspect, the routing platform 102 can essentially manage different VLANs (virtual LANs), e.g. a VLAN for voice on user plane, a VLAN for control signaling Iur, a VLAN for control signaling sent back to core network. In one example, the routing platform 102 can facilitate bandwidth management for the different VLANs. During provisioning, QoS (quality of service) and/or queuing functions can be determined and/or set that can facilitate management of content.

The routing platform 102 can be typically employed to facilitate user plane connections and most any handovers (e.g. soft handovers) internally within the mesh without accessing the core network. Accordingly, bandwidth going out of the mesh is merely for control signaling and thus traffic on the backhaul network can be substantially reduced. It can be appreciated that although wired ports are shown on the routing platform 102, the links can be wireless. The routing platform 102 can be easily programmed to communicate wirelessly with multiple femtos 104 rather than routing cables to connect each femto to the routing platform 102. Further, the backhaul can also be wireless. Furthermore, multiple femtos can be deployed in the mesh network to achieve redundancy such that if any one of the femtos fails, other femtos connected to the routing platform can be employed. Thus, the mesh network can be self-healing (as described in detail with respect to FIG. 3 infra).

Figure 2:
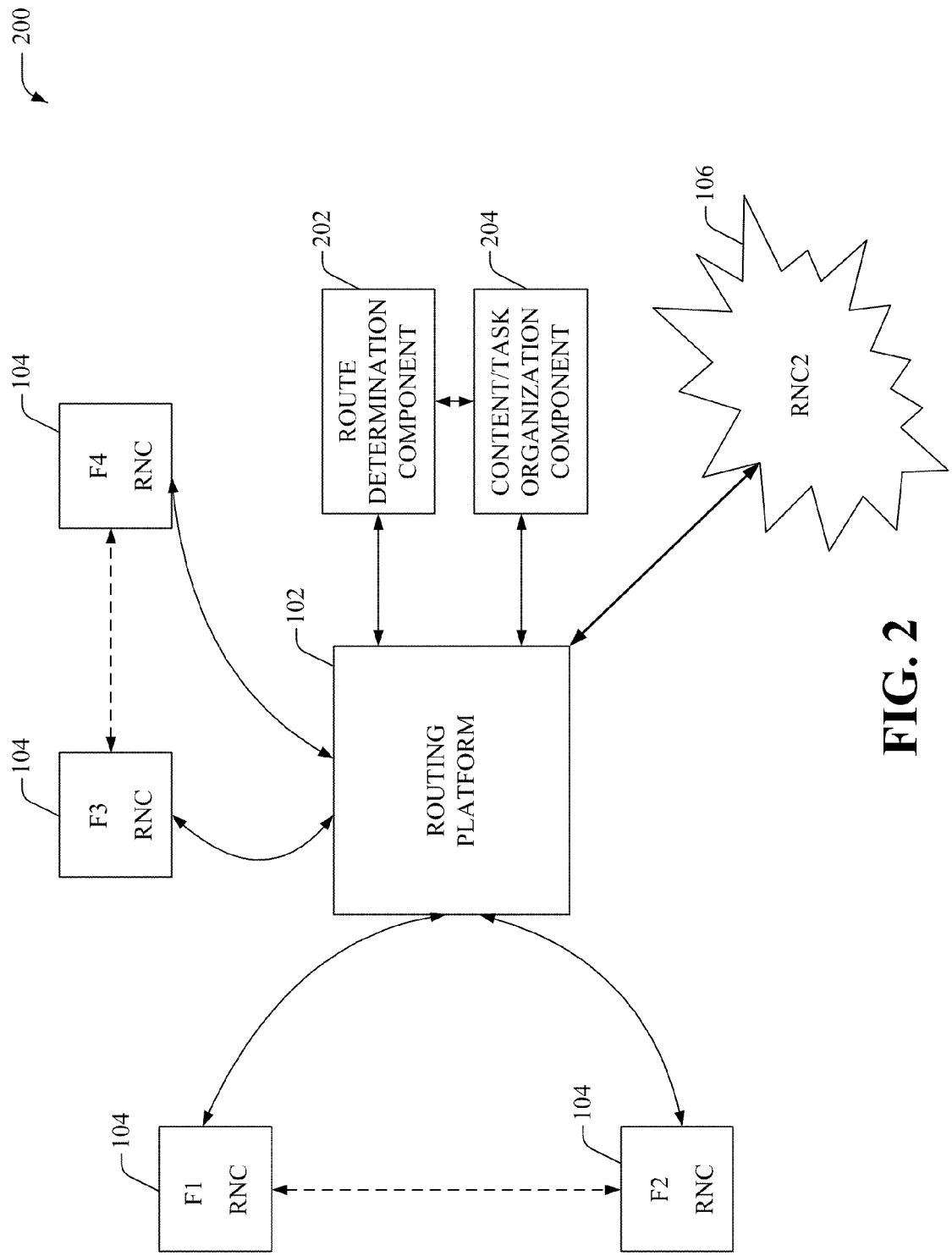
FIG. 2 illustrates an example system that can be employed to facilitate content and/or task organization within an enterprise femto network in accordance with an aspect of the disclosure.

Referring now to FIG. 2, there illustrated is an example system 200 that can be employed to facilitate content and/or task organization within an enterprise femto network in accordance with an aspect of the disclosure. The system 200 provides facilitates routing content between different nodes in the enterprise femto network without accessing the core network. It can be appreciated that the routing platform 102, femtos 104, and RNC2 106, can include functionality, as more fully described herein, for example, with regard to system 100.

The routing platform 102 can be employed to connect multiple femtos 104, for example, located within a building, office, hospital, hotel, airport, park etc. Specifically, the routing platform 102 connects the RNCs of the femtos 104 to each other and to an RNC2 106 associated with a femto gateway. The routing platform 102 can direct a packet received from a femto 104 based in part on routing information. Typically, a route determination component 202 can be employed to provide routing information. Further, transfer of content and/or tasks within the enterprise femto architecture can be managed by the content/task organization component 204. It can be appreciated that the route determination component 202 and/or the can be content/task organization component 204 connected to or embedded within the routing platform 102 (as described in detail with respect to FIG. 5 infra).

In one aspect, the route determination component 202 can facilitate organization of tasks associated with routing, such as, but not limited to, data transfers, point-to-point calls etc. Moreover, the route determination component 202 can aggregate data from the multiple femtos 104 to facilitate determination of UEs that are currently connected to each femto. Further, the route determination component 202 can analyze a communication packet received by the routing platform 102 from a femto 104. The analysis can be based on different techniques, such as, but not limited to, analysis of a destination address, source address, type of packet, type of protocol, one or more user (service provider, end user) defined rules or policies and/or user preferences. The route determination component 202 can also employ aggregated network data for analysis. Based in part on the analysis the route determination component 202 can determine whether the packet can be routed within the femto enterprise without transferring the packet to the core network. For example, when a user A connected to femto F1 initiates a voice call to a user B connected to femto F3, the routing platform 102 can receive a communication packet from femto F1 and the route determination component 202 can analyze the packet to identify that the recipient, user B, is connected to femto F3 within the femto enterprise. Thus, the packet can be routed internally without accessing the core network. Accordingly, the route determination component 202 can provide routing information to the routing platform 102 that indicates internal routing of the packet from F1 to F3.

The content/task organization component 204 can be employed to facilitate transfer of content and/or information associated with tasks within the femto architecture, such that, the core network is not accessed. For example, content from a device attached to femto F1, can be transferred to a device attached to femto F2 via the routing platform 102. Further, the content/task organization component 204 can facilitate, automatic synchronization of information in devices attached to different femtos in the enterprise network, such that core network is not accessed. For example, the content/task organization component 204 can facilitate automated synchronization of calendar, contacts list, etc., when the device attaches to a femto and/or can update tasks to be performed on devices connected to disparate (or same) femto. In one aspect, the content/task organization component 204 can synchronize content based at least in part through access privileges determined via access list(s), for example, white lists. As another example, content that is purchased and downloaded to the femto enterprise network can be accessed by or transferred to most any device attached to a femto in the femto enterprise network, without the device requiring to purchase and/or download the content from the core network.

Figure 3:
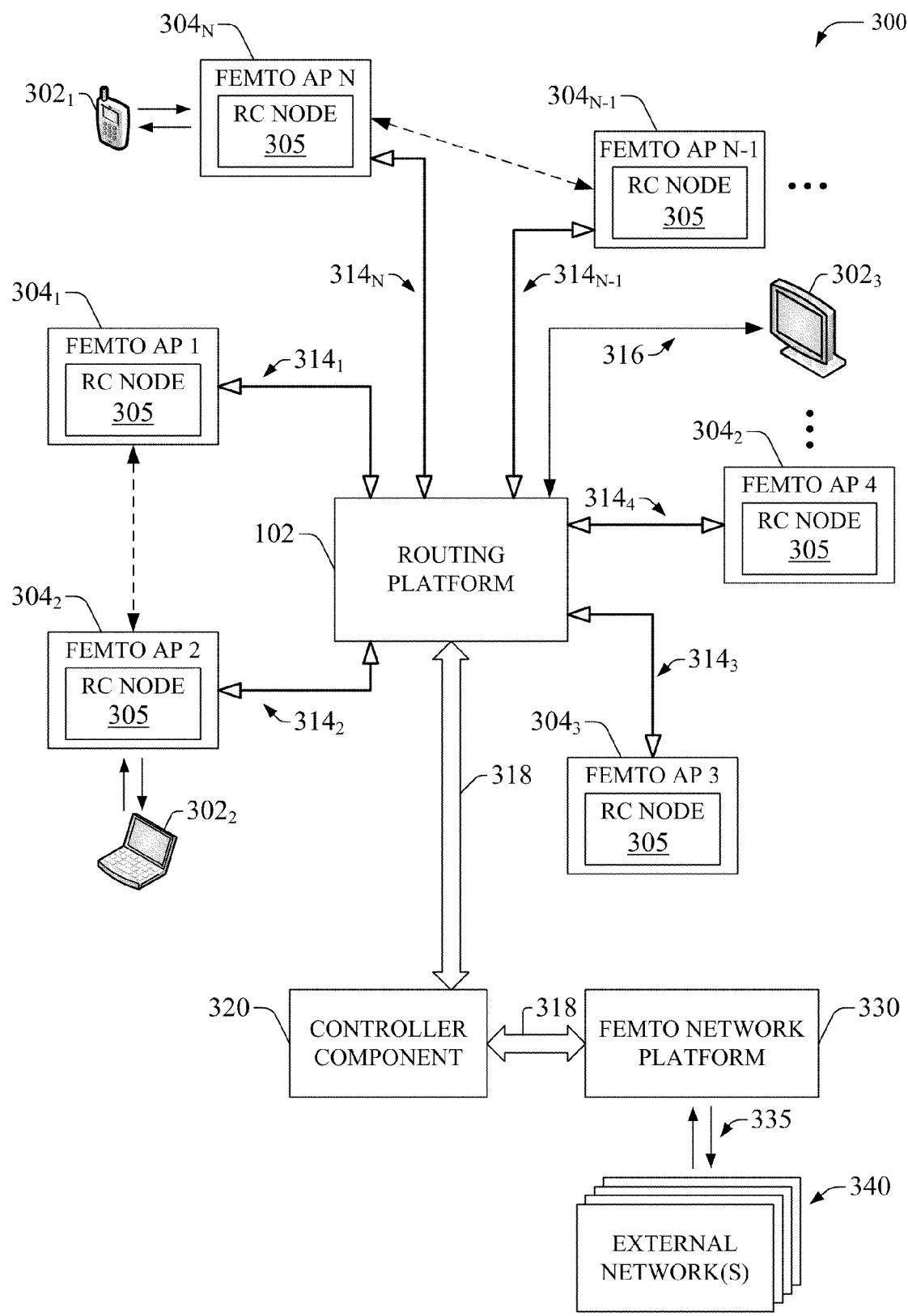
FIG. 3 illustrates a detailed diagram of an example enterprise femto network in accordance with aspects of the subject specification.

FIG. 3 illustrates a detailed diagram of an example enterprise femto network architecture 300 in accordance with aspects of the subject specification. A set of femto access points $304_1$-$304_N$, with N a natural number, can be functionally connected to a routing platform 102 that can be functionally coupled to a controller component 320, which can be operationally linked to a femto network platform 330. It can be appreciated that the routing platform 102 can include functionality, as more fully described herein, for example, with regard to systems 100 and 200. Further, femto access points $304_1$-$304_N$ can be substantially similar to femtos 104, and RC node 305 can be substantially similar to RNC of the femto 104, as described with respect to systems 100 and 200.

It should be appreciated that a single backhaul pipe 318 operationally connects routing platform 102 and controller component 320. Likewise, a single backhaul pipe 318 connects controller component 320 and femto network platform 330. In an aspect, femto network platform 330 can be functionally coupled, via one or more reference link(s) 335, to external network(s) 340, which can include service network(s) such as an internet protocol (IP) multimedia subsystem (IMS). In another aspect, in 3GPP UMTS radio technology, controller component 320 can be embodied in a radio network controller. It can be noted, although the controller component 320 is illustrated as a dedicated component, the controller component 320 can be part of the femto network platform 330 or a gateway node therein (not shown). In one example, the controller component 320 can be part of one of the external network(s) 340. It should further be appreciated that example enterprise femto network architecture 300 enables femto APs $304_1$-$304_N$ to be mutually connected, via routing platform 102, in a mesh network configuration, also termed herein as a mesh femto network. The portion of the enterprise femto network within the coverage area spanned by femto APs $304_1$-$304_N$ is private as opposed to public such as a macrocell network.

The number of femto APs $304_\lambda$, with $\lambda=1, 2 \ldots N$, connected to the routing platform 102 can be based at least in part on at least one of a number of ports on or bandwidth available to routing platform 102. Femto APs $314_\lambda$ are functionally connected to routing platform 102 through links $314_\lambda$, which can be broadband, backhaul wired links (e.g., optical fiber backbone, twisted-pair line, T1/E1 phone line, a digital subscriber line (DSL) either synchronous or asynchronous, an asymmetric ADSL, or a coaxial cable . . . ) or a wireless (line-of-sight (LOS) or non-LOS) links. Backhaul link(s) 318 also can wired or wireless. In an aspect, in 3GPP UMTS radio technology, a link $314_\lambda$ can be embodied in at least one of an Iur interface or an Iuh interface. It can be noted that the number of channel elements of a link $314_\lambda$ can be lower that the number of channel elements in backhaul link 318. Thus, the plurality of femto APs $304_1$-$304_N$ can be served via femto network platform 330, through single backhaul pipes 318, with less backhaul resources than in a conventional system in which a backhaul pipe 318 is functionally connected to each femto AP $304_1$-$304_N$.

Femto APs $304_1$-$304_N$ can be deployed within a confined coverage area, which can include either a single-floor or multi-floor facility or enterprise. Deployment plan generally minimizes dead spots and includes a number of femto APs sufficient to achieve operational redundancy, such that if one or more of the provisioned femto APs fails, disparate additional femto AP(s) functionally connected to routing platform 102 can be employed for communication. Thus, the mesh femto network can be self-healing. An enterprise can include, but is not limited to including, one of an office building; a residential complex, a business building such as department store, a bank, a restaurant, or a warehouse; a government facility; a school; a hospital; a hotel; a factory; an airport; a recreation or city park; or the like.

As illustrated in FIG. 3, each femto AP $304_\lambda$ (or femto APs illustrated in embodiments 400, 450 and 475 described infra), that is connected to routing platform 102 can comprise a radio controller (RC) node 305 that can include at least part of the functionality of a radio network controller. Routing platform 102 can functionally connect RC nodes 305 between two or more femto APs deployed within example femto enterprise network system 300. As indicated supra, link(s) $314_\lambda$ can include at least an Iur interface that can route packet stream(s) between the functionally connected two or more femto APs. An RC node 305 can have substantially the same functionality as that controller component 320. However, in one or more architecture(s) or embodiment(s), RC node 305 can have less complexity than controller component 320. Having an RC node 305 in each femto AP $304_\lambda$ can result in an optimal (e.g., sub-linear) or nearly optimal (e.g., linear) scaling of processing demand at routing component with respect to the number of provisioned femto APs in the femto enterprise network architecture. Processing demand in the femto enterprise network increases due to increased routing or scheduling processing. It can be noted that scheduling relates to scheduling of packet delivery rather than scheduling of radio resources, which is implemented by routing platform 102. When a femto AP is added to the femto mesh network 300, the RC node 305 associated with the femto AP can provide RNC functionality thereto and thus the mesh network. However, demand for backhaul resources, e.g., backhaul link 318, and controller component 320 does not grow with an increase in the number of femto APs functionally connected to routing platform 102. Accordingly, built-in RNC functionality can improve scalability with respect to a networked configuration in which routing platform also acts as a radio network controller.

In accordance with one embodiment, routing platform 102 can enable user plane connections directly, and can establish communication, e.g., exchange of voice or data and signaling, between two or more femto APs, e.g., femto AP $304_2$ and $304_N$. As discussed previously, routing platform 102 can enable communication between mobile devices, e.g., $302_1$, and $302_2$, attached to disparate femto APs, wherein traffic and signaling associated with the communication is routed within the example femto enterprise network 300 without delivery of data or management packets to femto network platform 330. For example, routing platform 102 can direct traffic generated by mobile device $302_1$, served through femto AP $304_N$ to wireless device $302_2$ served by femto AP $304_4$. Communication amongst mobile device $302_1$, and wireless device $302_2$ can be push-to-talk communication. Alternatively or additionally, routing platform 102 can allow push-to-talk communication between a mobile device and a pseudo-stationary tethered device such as $302_3$. It can be noted that, in an aspect, routing platform 102 is traffic agnostic in that a first device, mobile or otherwise, can operate in a first radio technology disparate from a second radio technology employed by a second device, mobile or otherwise, that communicates with the first device through routing platform 102 and via respective femto APs.

The routing platform 102 can direct a packet received from a femto AP, e.g., $304_{N-1}$, based in part on routing information (e.g. received from the route determination component 202 in FIG. 2). In an aspect, the routing information can indicate that the communication packet is to be transferred to femto network platform 330. Accordingly, routing platform 102 can perform a hard handover and direct the packet to femto network platform 330 through controller component 320. In another aspect, the routing information can indicate that the packet can be transferred internally from a first femto AP, e.g., $304_N$, to a second femto AP, e.g., $304_2$, functionally connected to routing platform 102. Moreover, in such case, routing platform 102 can perform a soft handover between a first femto AP ($304_2$) and a second femto AP (e.g., $304_3$) and establish communication such that dead spots or issue scenarios can be avoided and/or mitigated. Furthermore, routing platform 102 can determine control information, or signaling, for traffic routed directly between femto APs and route the control information, or signaling, to femto network platform 330 via controller component 320 through backhaul pipe 318.

Routing platform 102 also can enable communication of content(s), or traffic, among a device $302_3$ served primarily via a network that is part of external network(s) 340, such as one of a non-mobile broadband internet service network, a broadband digital cable network, or a macrocell network and mobile devices served through a femto AP $304_\lambda$. In an aspect, device 3023 can be an IP television (IPTV) tuner that can receive caller identification information when a call directed to a mobile device $302_1$ is received by routing platform 102. Such a feature can advantageously to alert a subscriber in a residence wherein the subscriber is associated with the mobile device $302_1$ and separated there from while the subscriber utilizes device $302_3$. In another aspect, when the enterprise is a wholesale store, or big-box store, device $302_3$ can be a voice-over-IP (VOIP) transceiver in a customer service platform which routing platform 102 can connect to a mobile device, e.g., $302_2$, served through a femto AP, e.g., $304_2$, within the enterprise femto network system 300 in order to provide customer assistance to a consumer associated with the mobile device. User equipment (UE) that operates within example enterprise femto network system 300 can include almost any or any electronic device that can connect wirelessly to a femto AP or can be linked operationally to a port within the routing platform 102. In addition to example UEs provided supra, user equipment can include mobile phones; media players; digital cameras; digital media recorders such as digital video recorders (DVRs); laptop computers; personal digital assistants (PDAs); personal computers; printers; scanners; digital photo frames; navigation device such as a global positioning system (GPS) module; gaming modules; and so forth. Further, it can be appreciated the UEs can be mobile, stationary, or pseudo-stationary, and wireless or tethered.

In an aspect, during internal communication within the enterprise femto architecture 300, routing platform 102 can establish and retain a control link to femto network platform 330, e.g., to gateway node(s) therein, that can be employed by femto network platform 330, via a billing server, to process billing charges; it should be appreciated that billing processing can be effected by an application layer within one of external network(s) 340 such as an IMS network.

At least an advantage of example femto enterprise architecture 300 is that it reduces at least one of backhaul network traffic or signaling among provisioned femto APs that are part of the femto enterprise network and a femto network platform, which can include controller node 320. At least another advantage of example femto enterprise architecture 300 is that routing can be self-healing; for instance, traffic can be routed via an alternative femto AP when an intended femto AP is non-functional or radio communication thereby is otherwise impaired. In addition, data and signaling can be cached or recorded for subsequent utilization to mitigate, at least in part, communication disruption. At least a further advantage of example enterprise femto network architecture 300 is that it can mitigate utilization of private branch exchange (PBX), or internet protocol (IP)-PBX, resources for intra-premises communication, or communication among a mobile device served through a femto wide radio access network, or a wide area network, which can be mobile or otherwise.

Figure 4A:
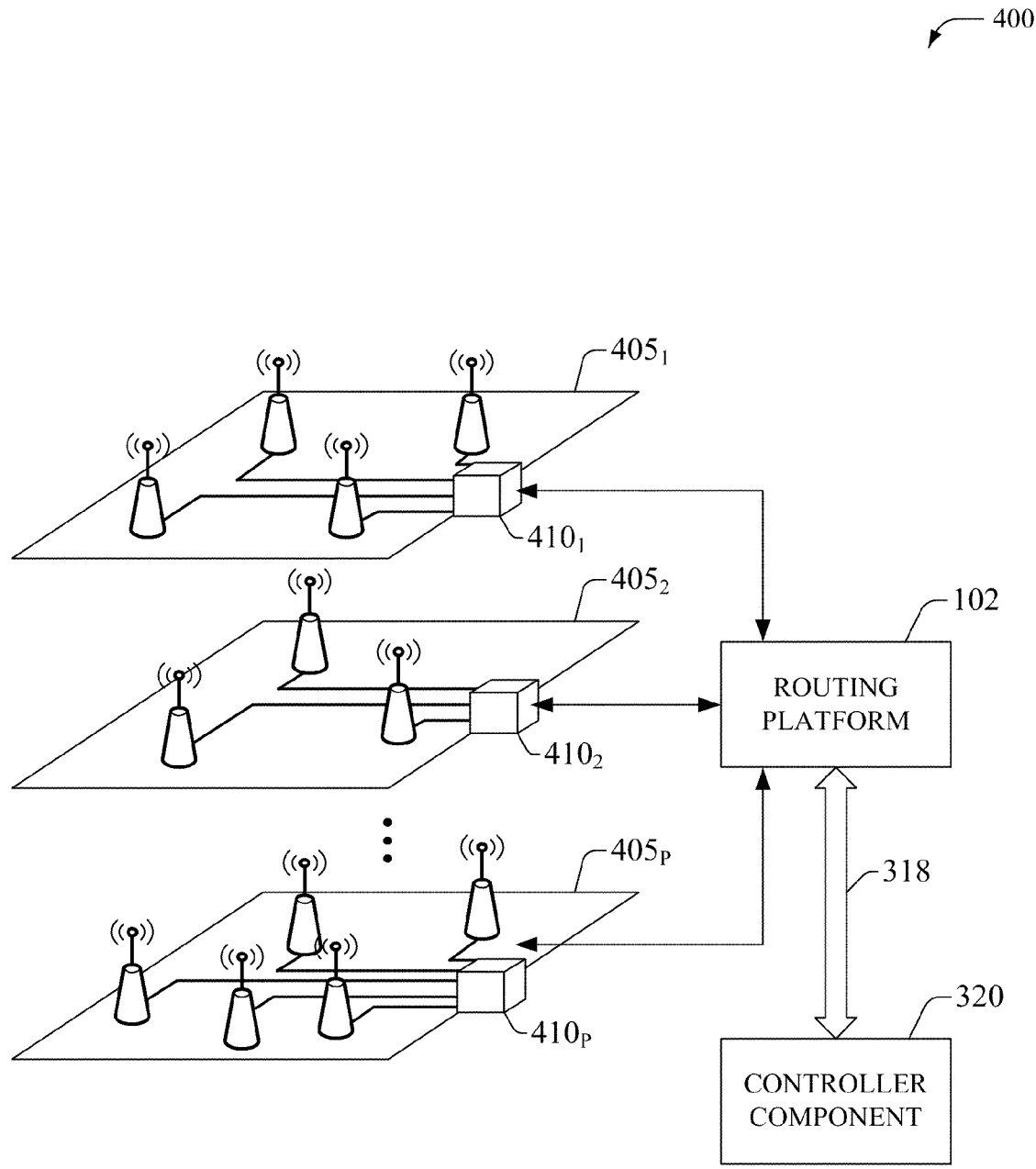
FIGS. 4A, 4B and 4C illustrate, respectively, a block diagram of an example multi-coverage-area femto mesh network, a block diagram of a femto mesh network in which routing in a multi-loci environment is decentralized and a femto mesh network wherein various routing platforms related to various enterprise deployments are multiplexed, in accordance with aspects described herein.

Referring now to FIG. 4A, there illustrated is an example block diagram of an example multi-coverage-area femto mesh network 400 in accordance with aspects described herein. Coverage areas, $405_\mu$ ($\mu=1, 2 \ldots P$) can include indoor environments such as floors in a building and, at least partially, outdoor environments such as parking lots; terraces, decks, or verandas; or sports fields or courts. In each coverage area $405_\mu$, a network interface device (NID) $410_\mu$ centralizes broadband link(s), illustrated as thick lines without arrowheads (for clarity), from each deployed femto AP. NIDs $410_\mu$ can be functionally connected to routing platform 102. It can be appreciated that the routing platform 102 and controller component 320 can include functionality, as more fully described herein, for example, with regard to systems 100, 200 and 300.

Deployed femto APs can be further connected to a single backhaul pipe 318 through routing platform 102. Routing platform 102 can direct traffic among wireless devices located in disparate coverage areas. It is noted that routing functionality provided by routing platform 102 can be centralized. As an example, consider a scenario in which the example enterprise femto network architecture 400 is deployed in a multi-floor building wherein multiple femto APs can be deployed on each floor, e.g., coverage area $405_\mu$, of the building. In this example, a mobile device on a first floor, e.g., $405_2$, connected to a femto AP on the first floor can establish communication (e.g., voice or data) with another mobile device on a second floor, e.g., $405_P$, connected to a femto AP therein, without accessing a femto network platform linked to controller component 320.

Figure 4B:
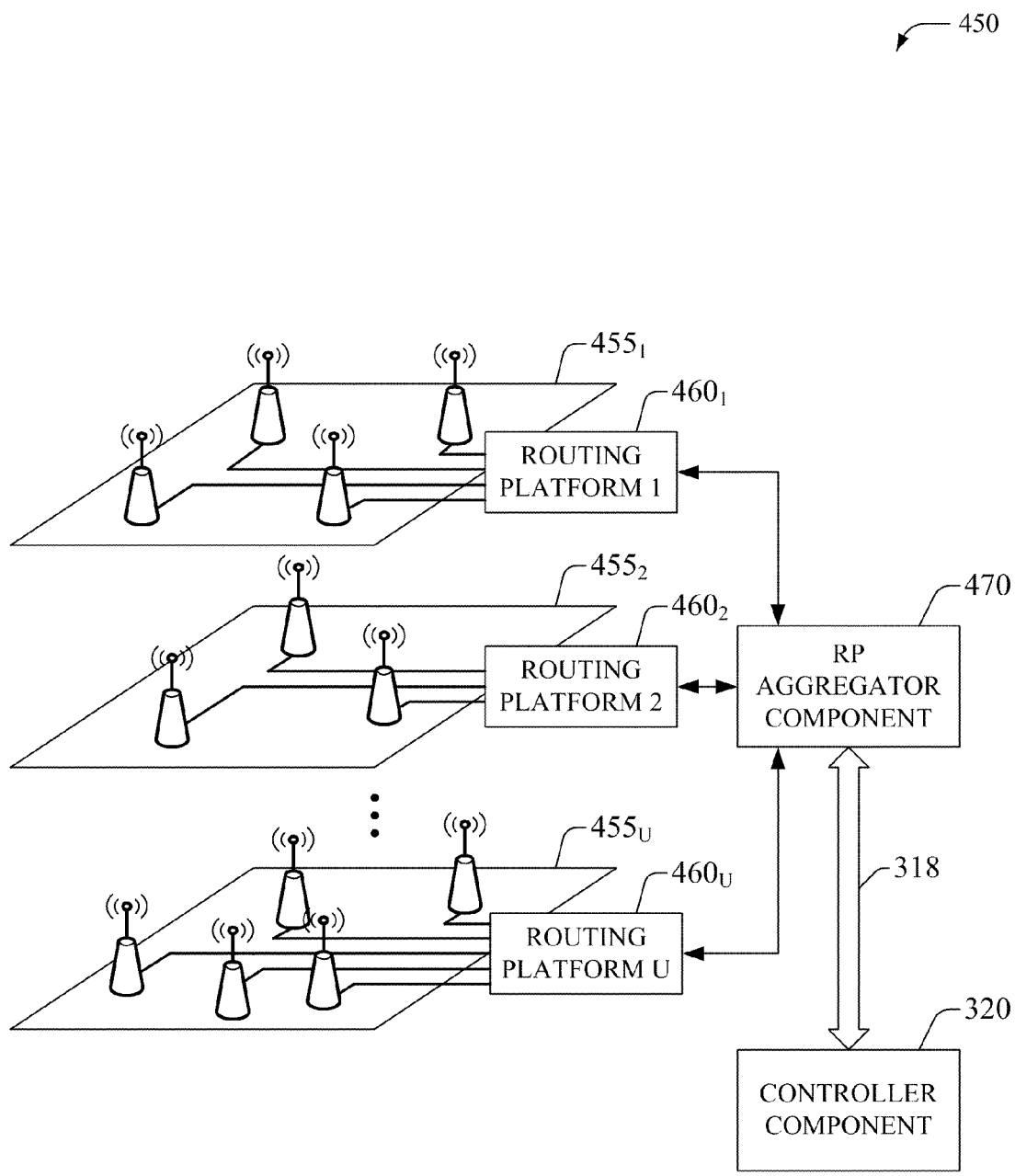

Alternatively or additionally, FIG. 4B illustrates an example block diagram of an example femto mesh network 450 in which routing in a multi-coverage-area environment is decentralized, effected by a set of routing platforms $460_1$-$460_U$, U is a natural number, and each coverage area $455_\gamma$, with $\gamma=1, 2 \ldots U$, linked to each routing platform in the set. It can be appreciated that each routing platform $460_1$-$460_U$ is substantially similar to routing platform 102. Moreover, a RP (routing platform) aggregator component 470 interfaces the multi-area femto enterprise network architecture 450 with controller component 320. The multiple routing platforms $460_\gamma$ can communicate with each other such that configuration information with respect to femto APs associated with each routing platform and devices operationally connected to the femto APs is available to each routing platform $460_\gamma$; configuration information can enable, at least in part, internal routing of traffic. The RP aggregator component 470 can operate as at least one of a pass-through element or as a traffic shaping component, preserving QoS in accordance with predetermined QoS profile(s) for various types of traffic or signaling. As illustrated, one routing platform $460_\gamma$ is deployed on each coverage area $420_\gamma$, with $\gamma=1, 2 \ldots U$, wherein each coverage area can be a floor of a building (e.g., an office building, a school, a department store) and routing platforms $460_\gamma$ on each floor can be mutually functionally connected to create an enterprise femto mesh network structure that can cover the entire building. It is noted that based at least in part on the size of a coverage area $455_\gamma$, more than a single routing platform can be deployed in the coverage area $455_\gamma$. Multiple femto APs can be functionally connected to a single routing platform $460_\gamma$, and multiple routing platforms $420_1$-$420_U$ can be connected together to create a larger mesh femto network.

Processor(s) (not shown) can provide at least part of the functionality of RP aggregator component 470. To operate or confer at least in part functionality to the RP aggregator component 470, the processor(s) can store information in, and retrieve information from, a memory (not shown). The information can include at least one of code instructions, data structures, program modules, or the like.

Figure 4C:
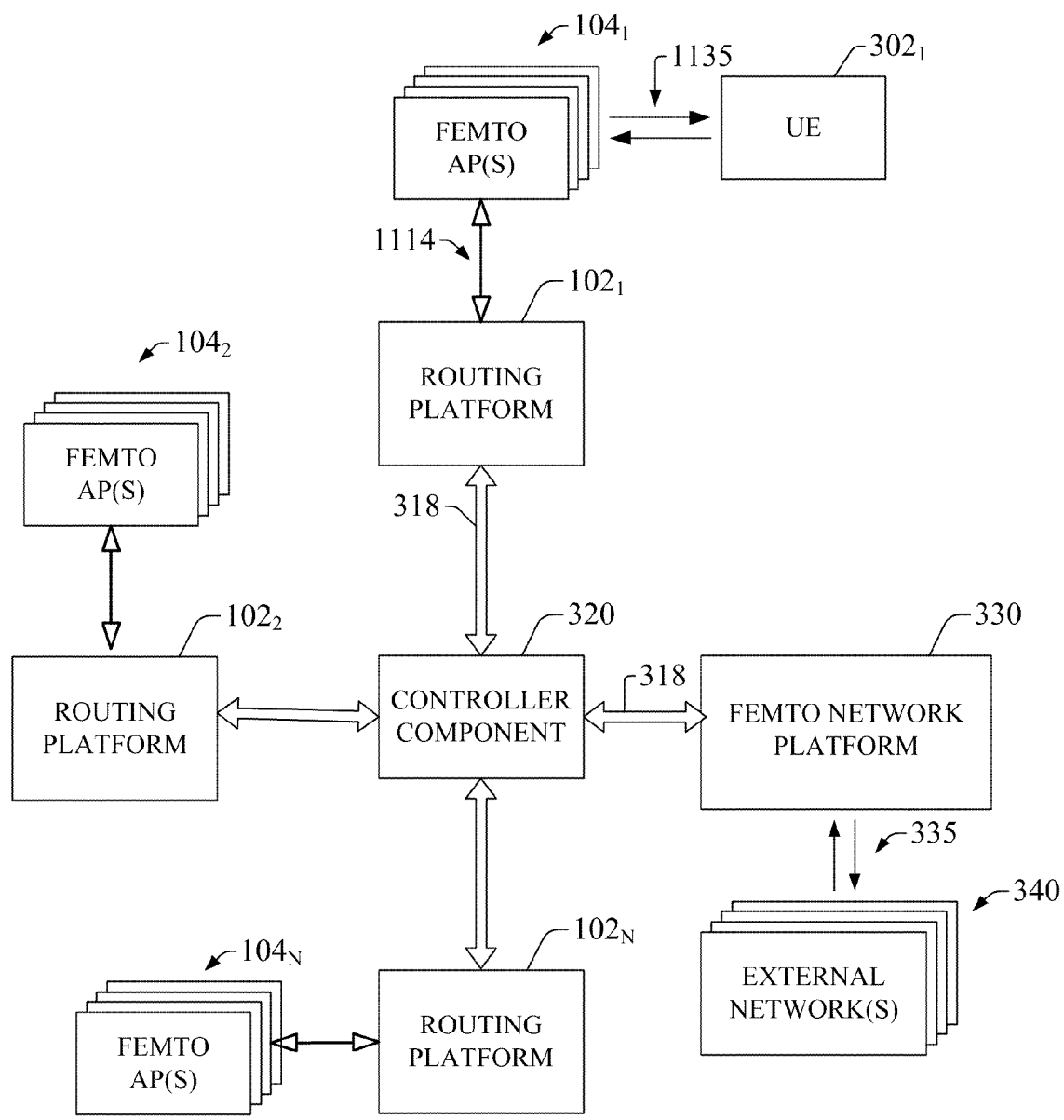

Further, FIG. 4C illustrates an example femto mesh network 475 wherein various routing platforms related to various enterprise deployments can be multiplexed by employing a single controller component 320. According to an aspect, a controller 320 can receive information from a set of routing platforms, $102_1$-$102_N$, wherein N is a natural number. Each of the routing platforms $102_1$-$102_N$ can be connected to multiple femto APs $104_1$-$104_N$, which facilitate connectivity to/from UEs $302_1$ connected to the respective femto APs $104_1$-$104_N$. As discussed previously, each routing platform $102_1$-$102_N$ can receive data from a UE attached to a femto AP $104_1$-$104_N$ within the enterprise femto architecture. Moreover, the routing platform $102_1$-$102_N$ can perform an analysis to determine information associated with routing of the received data (e.g. source address, destination address, etc.). Further, a route can be determined for transferring the packet from the routing platform based in part on the analysis and/or user defined rules or policies and/or user preferences. In particular, the routing platform $102_1$-$102_N$ can determine whether a soft or hard handover can be performed. When a hard handover is to be performed, the routing platform $102_1$-$102_N$ can route the data to the femto network platform 330 via the controller component 320. The controller component 320 can typically include functionality of a second RNC or most any other network management component associated with the femto network platform 330, which can be embodied in a FGW. In an aspect, the controller component 330 can multiplex a set of routing platforms $102_1$-$102_N$ related to various enterprise deployments (e.g. as illustrated in FIG. 4A, 4B).

In an example embodiment, scheduling of radio resources associated with femto APs $104_1$-$104_N$ can be implemented by respective routing platforms $102_1$-$102_N$. Accordingly, when a new femto AP is added to the femto mesh network 475, an RC node (not shown) associated with the new femto AP can provide RNC functionality thereto and thus the mesh network 475. However, demand for backhaul resources, e.g., backhaul link 318, and controller component 320 does not grow with an increase in the number of femto APs functionally connected to each routing platform $102_1$-$102_N$. Moreover, since the routing platforms $102_1$-$102_N$ implement radio control over radio resources associated with wireless service supplied by the provisioned femtos within the enterprise, the controller component 320 is not affected by a change in number of femto APs $104_1$-$104_N$ associated with routing platforms $102_1$-$102_N$. Accordingly, the femto mesh network 475 enables advantageous deployment scaling, since addition of one or more femtos APs $104_1$-$104_N$ to the enterprise does not result in additional processing load at the controller component 320.

Figure 5:
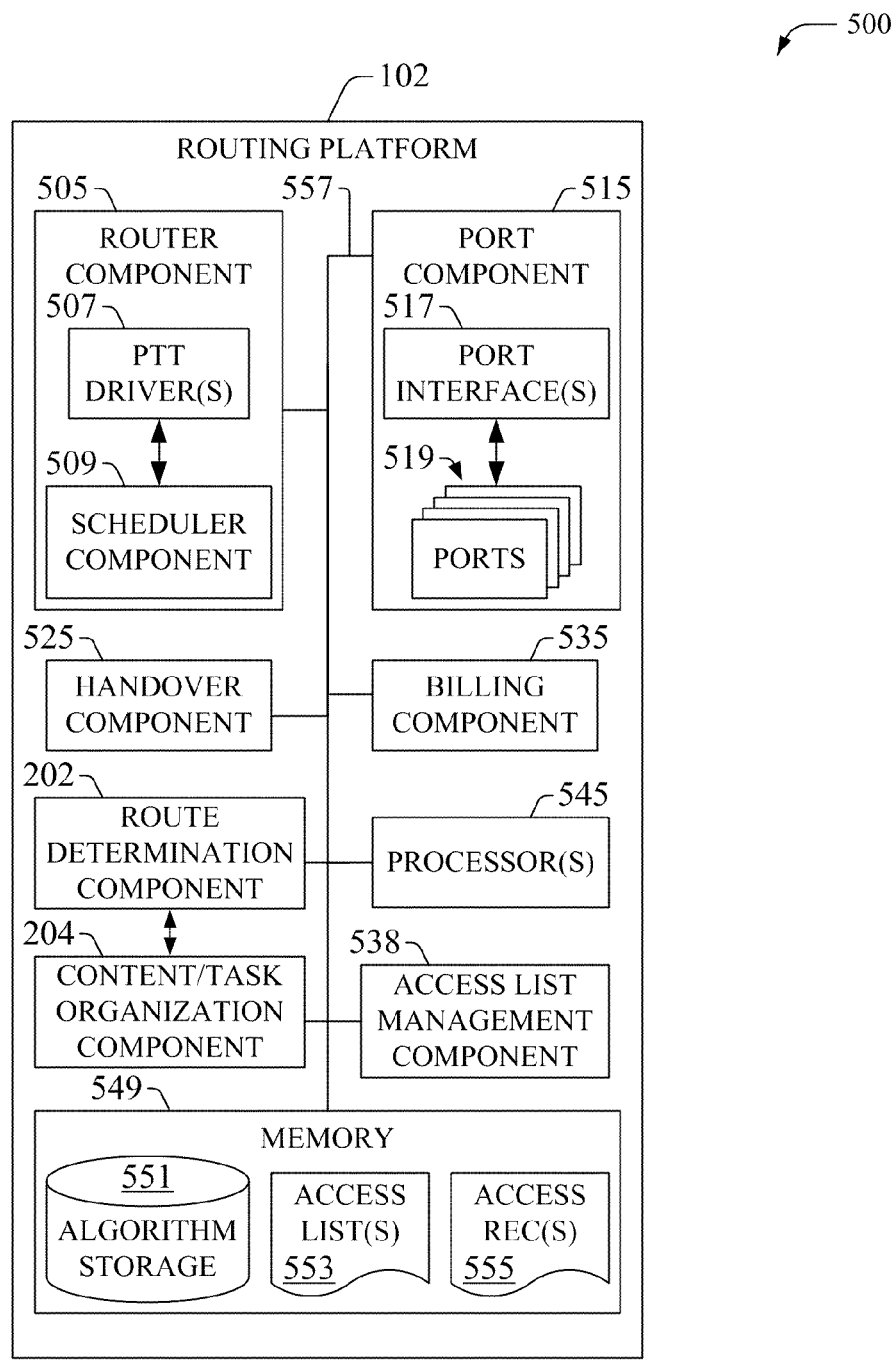
FIG. 5 displays a block diagram of an example embodiment of a routing platform that is part of an enterprise femto network architecture in accordance with aspects disclosed herein.

Referring now to FIG. 5, there illustrated is an example system 500 that facilitates routing of information from multiple femto access points within an enterprise femto architecture, according to an aspect of the subject disclosure. Typically, connections amongst backhaul links ($314_\lambda$) and routing platform 102, NIDs ($410_\mu$) and routing platform 102, and routing platform 102 and RP aggregator component (470) can be effected through a port component 515 within the routing platform 102, as illustrated in example embodiment 500. Port component 515 can include port interface(s) 517 to configure one or more of ports 519, which can include parallel ports (e.g., GPIB, IEEE-1284), serial ports (e.g., RS-232, V.11, USB, FireWire or IEEE-1394 . . . ), Ethernet ports, V.35 ports, X.21 ports, or dry contacts, or the like. Port interface(s) 517 can include a wireless interface such as a wireless card and associated circuitry to implement telecommunication. In addition, port interface(s) 517 can include one or more physical docks that support physical connectors for respective ports 519. Routing platform 102 can be configured, or programmed, to communicate wirelessly with one or more femto AP ($304_\lambda$) rather than through routing cables. Configuration can be accomplished trough a display interface (not shown) that enables data entry in routing platform 102, or through a device such as a computer, mobile or otherwise, connected to port component 515.

In one aspect, routing component 102 can include push-to-talk driver(s) 507 to enable at least in part point-to-point communication among one or more devices, mobile or otherwise in the femto mesh network. In view of such internal communication, for outgoing communication(s) off the example mesh femto network, routing platform 102 can allocate bandwidth primarily for control, or signaling, and thus traffic on the backhaul network can be substantially reduced. In addition, such communication internal to the example enterprise femto network system can reduce communication delay, with ensuing improvement of perceived QoS for latency-sensitive content such as multiplayer gaming.

According to an embodiment, routing platform 102, via router component 505, can receive carrier-frequency information associated with channels employed for telecommunication within the coverage area of an enterprise femto network. Router component 505 can aggregate carrier-frequency data to form a carrier-frequency map. In an aspect, the carrier-frequency map can enable load balancing of traffic within the enterprise femto network through dynamic allocation of bandwidth to specific femto APs functionally connected to the routing platform. Scheduler component 509 can signal a bandwidth allocation to a femto AP within the enterprise femto network.

In an example embodiment, the router component 505 can direct traffic and signaling among a set of deployed femto APs, e.g., femto APs $304_1$-$304_N$ in FIG. 3. Traffic can be routed in accordance at least in part with a set of one or more algorithm(s) retained in memory element 549. Router component 505 can determine a near-optimal or optimal route for a received data or management packet, to avoid network congestion within mesh femto network. In addition, router component 505 also can configure point-to-point communication as part of routing functions based at least in part on channel conditions. Moreover, router component 505 can utilize configured access list(s) 553 to route traffic and signaling and ensure data integrity or self-healing routing. Furthermore, router component 505 can include the scheduler component 509 to establish quality of service (QoS) for communication among two or more devices in accordance at least in part with at least one of traffic priority profile or QoS class (e.g., best effort, maximum bit-error-rate (BER), guaranteed data rate). In an aspect, during provisioning of a femto AP, which can be effected by a provisioning server within femto network platform (330), scheduler component 509 can determine or configure at least one of quality of service (QoS) or one or more queuing functions that can facilitate management of content(s), e.g., traffic or signaling. Scheduler component 509 also can employ load-balancing techniques, which can be implemented through algorithms retained in algorithm storage 551, to enable efficient network or resource(s) utilization.

In addition, scheduler component 509 can utilize access list(s) 547 that control access to one or more femto APs by one or more mobile device to route traffic, e.g., a data packet, and signaling, e.g., a management packet, amongst femto APs in the enterprise femto architecture. In an aspect, access list(s) 547 can allow access to a femto AP, e.g., the access list is a white list, or can include black list(s), which can explicitly determine mobile devices that are denied access to service through one or more femto APs and trigger an exception handling subsequent to attachment attempt(s) effected by black listed mobile devices. In an aspect, exception handling can include authorization of attachment to a femto AP and notification of an authority, as discussed below. Further, memory 549 can include access record(s) 555 that can be utilized to keep track of devices that have accessed specific femto APs within the enterprise network. Such device need not be whitelisted, they can be blacklisted devices. Moreover, the tracking feature can allow security aspects and generation of access logs to the enterprise network. As an example, when a mobile device is authorized, the attachment is recorded, e.g., as part of access record(s) 355, and an attachment report can be conveyed. Typically, the attachment report can deliver registration information such as a time stamp, UE identifier codes or tokens, or the like. Alternately, when the mobile device is not authorized, it can be established whether the mobile device is a blacklisted device and in an affirmative case, exception handling can be implemented.

To perform almost any or any handover (e.g., soft handover) internal to example mesh femto network without accessing femto network platform (330), e.g., delivering signaling or traffic thereto, routing platform 102 also can configure and exploit user-plane connection(s). In an aspect, routing component 102 can exploit links ($314_\lambda$), e.g., Iur interfaces, between femto APs ($304_\lambda$) to enable soft handover. As illustrated in example embodiment 500, routing platform 102 can include a handover component 525 to administer handoff of a wireless device served by a first femto AP to a second femto AP in the femto enterprise network architecture. Handover component 525 can implement hard handoff or soft handoff in accordance at least in part with a set of handover criteria (not shown), which can be configurable by a wireless service provider on an event basis or as a function of time. In an aspect, soft handover can be effected at least in part based on at least one or more RF boundaries, which can be configured through a timing component, as discussed below. In example embodiment 500, memory 549 can retain handover criteria (not shown in FIG. 5).

In another aspect, routing platform 102 can include access list management component 538 which can generate or modify, at least in part, access list(s) 553 (e.g., whitelist(s) or blacklist(s)) based at least in part on signaling received from one or more femto APs within the set of femto APs deployed as part of the femto enterprise network. Access list(s) 553 generated through access list management component 538 can be active for a predetermined period, and after such period elapses can be deleted, either logically or physically, based at least in part on signaling received from one or more network components. Signaling can include mobile device identifier attribute(s). Access list management component 538 can either accept or reject such attribute(s) based at least in part on a set of criteria (not shown) which can be retained within memory 549. Further, for accepted mobile device identifier attribute(s), a default or initial level of access; for instance, almost all or all femto APs deployed as part of enterprise femto network can provide service to an identified mobile device. Default or initial level of access can be modified subsequently based at least in part on additional signaling received by routing platform 102. As an illustration, the set of acceptance or rejection criteria can include at least one of the following. (i) Valid mobile device identifier, e.g., wireless device numbers such as IMSIs, MSISDNs, or other codes or tokens. (ii) Active mobile device identifier or identifier flagged for update; e.g., an identifier that corresponds to an old phone number that is to be updated to a current number. (iii) Status of election (e.g., opt in) or non-election (e.g., opt out) flags for inclusion in a whitelist, wherein status is conveyed, for example, via a K-bit word (K is a natural number) within an entry for the mobile device in a subscriber database. (iv) Operational capabilities of the identified mobile device (e.g., wireless technology utilized by the device such as second generation (2G), third generation (3G), or fourth generation (4G) technologies, radio frequency bands in which the mobile device can receive communications . . . ). (v) Commercial standing of the identified mobile device; e.g., good standing or outstanding bill payments, hotlined mobile device in view of recurring lack of timely payments for service, stolen device . . . ; or the like.

In addition the routing platform 102 can include a billing component 535 that can allow to establish the control link and convey it to a femto network platform (330) to update a billing database associated with a billing server that can apply, for example, different charges for internal communication within the enterprise femto network architecture and external communication with femto network platform 330. Charges associated with internal communication can be lower than charges associated with external communication. The control link also can be retained in memory 549, e.g., in a buffer (not shown), within routing platform 102 such that if a failure occurs in femto network platform (330), internal communication within the mesh femto network can continue uninterruptedly. Retained control data can be transferred to femto network platform (330) for billing purposes when it resumes operation(s).

As discussed previously with respect to FIG. 1, the example enterprise femto network system can afford multiple billing schemes associated with a wireless service provider that administers the example femto network architecture. As an example, billing schemes can be retained in memory 549. In an aspect, the one or more billing schemes can be dictated, at least in part, by access configuration(s) retained in access list(s) 547. It is to be appreciated that the subject specification can configure and employ most any billing scheme, as described with respect to system 100 and is not limited to the aforementioned illustrative billing scheme(s). In one aspect, the wireless service provider can configure or predefine billing charges based at least in part on criteria such as served customer segment, an implemented promotional campaign, marketplace, operational costs, or the like. In example embodiment, the billing component 535 can configure, at least in part, and implement one or more billing schemes for served traffic within femto enterprise femto network architecture or for traffic delivered to or received from a femto network platform. In addition, billing component 535 can modify such configured billing charges dynamically, e.g., as a function of time, based at least in part on operational conditions such as available network bandwidth, load of one or more deployed femto APs within an enterprise femto network system, volume of traffic manipulated by routing platform 102, or the like.

In an aspect, routing platform 102 can manage different virtual local area network(s) (VLAN(s)) such as one or more of a VLAN for voice or data traffic on user plane; a VLAN for control signaling transported through at least a portion of link(s) ($314_1$), which can be embodied in an Iur interface; a VLAN for control signaling conveyed to femto network platform (330); or the like. In an example, routing platform 102 can enable bandwidth management for the different VLANs.

According to embodiment, routing platform 102 includes processor(s) 545 configured to confer, and that confers, at least in part, functionality to substantially any or any component within routing platform 102 in accordance with one or more aspects of the subject innovation. Processor(s) 545 is illustrated as external to the various functional elements or components of routing platform 102; however, processor(s) 545 can be distributed amongst such various functional elements or components. Processor(s) 545 is functionally coupled to each functional element or component and to memory 549 through bus 557, which can be embodied in at least one of a memory bus, a system bus, an address bus, or one or more reference link(s) or interface(s). Processor(s) 545 can store information in, and retrieve information from, memory 549 necessary to operate and/or confer at least in part functionality to each of the components that reside within routing platform 102. The information can include at least one of code instructions, data structures, program modules, or the like. According to an aspect, the routing platform can further include a route determination component 202 and/or the can be content/task organization component 204 that can include functionality as described herein, with respect to system 200.

Figure 6:
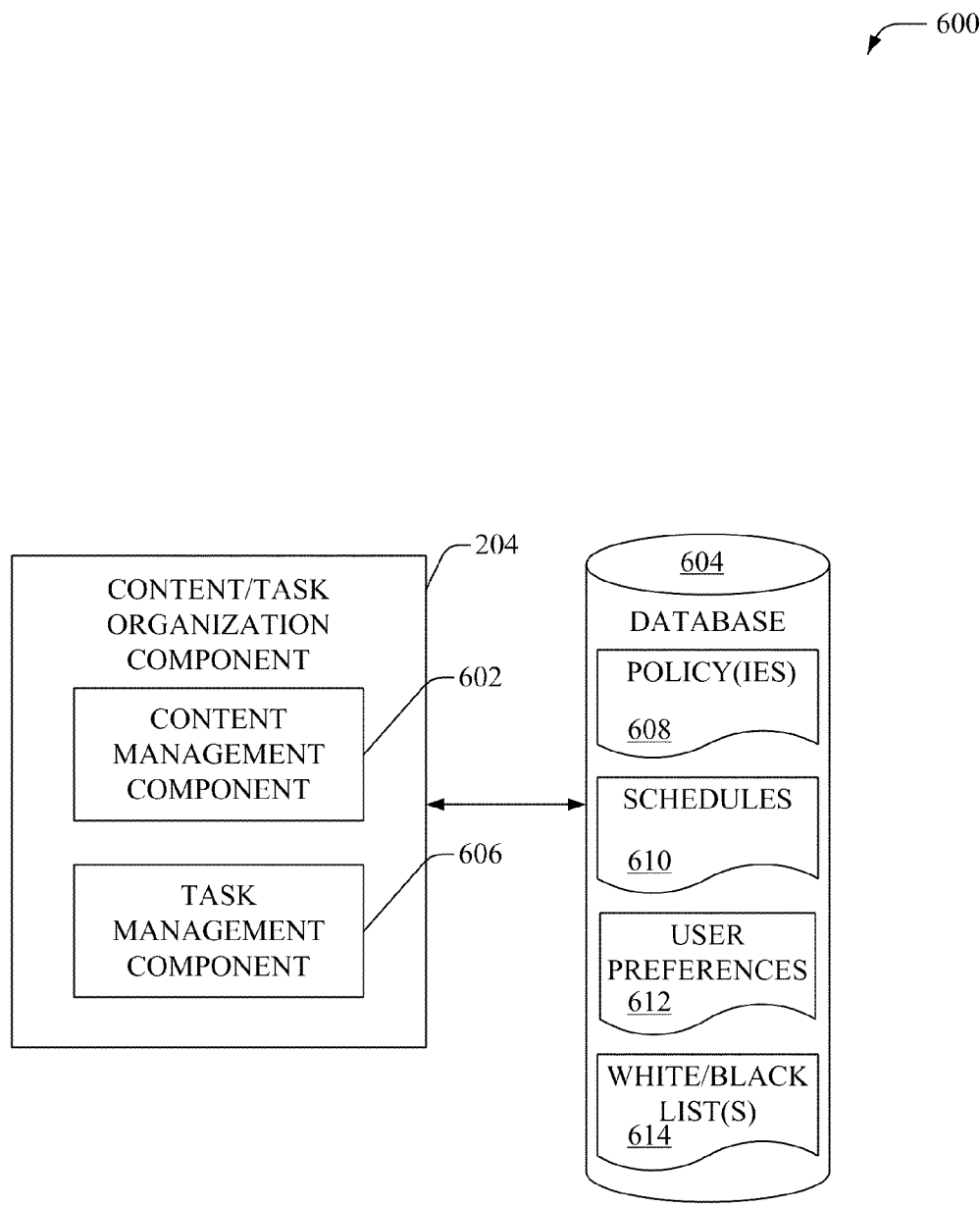
FIG. 6 illustrates an example system that can facilitate content and/or task management in a femto enterprise architecture in accordance with an aspect of the subject disclosure.

Referring to FIG. 6, there illustrated is an example system 600 that can facilitate content and/or task management in a femto enterprise architecture in accordance with an aspect of the subject disclosure. Typically, the content/task organization component 204 can facilitate content delivery and/or efficiently manage tasks within the enterprise femto, without accessing the core network. It can be appreciated that the content/task organization component 204 can include functionality, as more fully described herein, for example, with regard to system 200.

According to an aspect, the content/task organization component 204 can include a content management component 602 that can be employed to organize content within the femto enterprise. Moreover, the content management component 602 can facilitate management and/or organization of content between multiple devices attached to disparate femto access points (or the same femto access point) connected to the femto enterprise without accessing the core network. In one aspect, the content management component 602 can synchronize content between two or more devices connected to femto APs in the femto enterprise. In another aspect, content management component 602 can facilitate internal distribution of content between devices within the femto enterprise. It can be appreciated that the content management component 602 can employ one or more access lists (e.g., white lists) to synchronize and/or distribute content between devices. Typically, the billing charge associated with internal communication can be lower than the charge associated with external communication that utilizes the core network. Thus, the internal communication (e.g., synchronization, transfer, distribution of content) facilitated by the content management component 602 can contribute to reduced costs. It can be appreciated that content can be most any data, including, but not limited to, text, audio, video, image, etc. Further, the content can be streamed in real time or buffered during communication.

In accordance with one embodiment, the content management component 602 can be employed to distribute content downloaded from the core network. In one aspect, the content can be purchased from a content provider over the core network. Thus, once downloaded to the femto enterprise, the content can be distributed or transferred to multiple devices within the femto enterprise without accessing the core network and accordingly the charges associated with network usage can be substantially reduced. Moreover, the synchronization, transfer, distribution of content can be automated based in part on a policy 608, schedule 610, user preference 612 and/or white/black lists 614 stored in a database 604. As an example, the database 604 can be part of memory 549 (in FIG. 5). In one aspect, a femto enterprise can be deployed in a large home, such that multiple femto AP are utilized to cover the entire house. A user in the home can connect a home computer (e.g. PC, laptop, etc.) to a femto AP and access the core network to download content to the PC, for example, song. The content management component 602 can employ the information stored in database 604 (e.g. a policy 608, schedule 610, user preference 612 and/or white/black lists 614) to determine that the downloaded song can be transferred to a home audio system, a car music player, portable music players for each individual in the home, which can be connected to disparate femtos in the femto enterprise. The content management component 602 can instruct the routing platform (102 in FIG. 2) to transfer the song to the multiple devices. Accordingly, the routing platform can facilitate content transfer, and send a control link associated with the network usage to the core network for billing purposes. In addition, control data associated with billing information associated with content transfer can also be provided to the content provider, such that appropriate charges are applied.

As another example, a femto enterprise can be employed in a factory, wherein multiple femto APs deployed in the factory can be connected to a common routing platform. In this example, the content management component 602 can be employed to facilitate content transfer from a machine (e.g. an LTE based machine) connected to one femto AP to a mobile phone of an employee connected to a disparate femto AP. Thus, an employee in charge of the machine can receive updates on his mobile phone (e.g. via an SMS message) when the employee is at his desk or at any other location in the factory, such that, his mobile phone is connected to most any femto AP within the femto enterprise. The database 604 can store information that indicates updates from the machine can be transferred to the mobile phone of the employee. Further, the content management component 602 can identify a femto AP the mobile phone of the employee is currently connected to and can instruct the routing platform (102 FIG. 2) to route content from the machine to the mobile phone via the identified femto AP. The routing platform 102 can transfer content to the identified femto AP and send a control link associated with billing information to the core network. Additionally, if the content management component 602 identifies that the employee's mobile phone is not connected to the femto enterprise, the content management component 602 can instruct the routing platform to direct the content to a manager's mobile phone within the enterprise or to the employee's mobile phone via the core network, as per the specifications stored in the database 604.

According to yet another example, the femto enterprise can be employed in a university or school, such that a professor can transfer an assignment or class notes from a computer in the professor's office to all laptops or computers connected to a particular femto AP that has a coverage area of a classroom. Accordingly, the content from the professor's computer, connected to a femto AP can be routed to a disparate femto AP in the femto enterprise without accessing the core network. The content management component 602 can determine a destination femto AP based in part on an analysis of the information from database 604 and the content received at the routing platform (102 in FIG. 2) and can instruct the routing platform to direct content to the identified femto AP. Thus, the content can be delivered faster, without accessing the core network. It can be appreciated that, similarly, submissions can be sent from students' computers attached to most any femto AP in the enterprise, to a concerned professor's office computer attached to a disparate (or same) femto AP in the enterprise, without accessing a core network.

Referring back to FIG. 6, the content/task organization component 204 can further include a task management component 606 that can be employed to organize task information within the femto enterprise. In one aspect, the task management component 606 can synchronize, update, organize, etc. tasks and/or events associated with devices connected to multiple femto APs in the femto enterprise. Moreover, the task management component 606 can synchronize, update or organize calendars or contact lists associated with the devices. Specifically, the database 604 can store information, such as, but not limited to a policy 608, schedule 610, user preference 612 and/or access lists, such as, white/black lists 614 that can help the task management component 606 to perform operations.

In one example, the task management component 606 can be employed to synchronize task data on various devices in a factory, connected to disparate femto APs within the femto enterprise, without accessing the core network. For example, a device connected to femto A in the factory can indicate completion of a phase 1. Accordingly, the task management component 606 can update the event lists on various devices connected to disparate femtos in the femto enterprise. Typically, the task management component 606 can update devices (via the routing platform) associated with phases one and two, regarding completion of the first phase. Further, the task management component 606 can send messages (via the routing platform) to concerned employees. Thus, the communication (updates, synchronization, and/or organization) can be internal to the femto enterprise and accordingly only billing information associated with the communication can be sent to the core network.

In another example, the task management component 606 can facilitate organization of tasks, such as, but not limited to, chores, when the femto enterprise is employed in a large home. Thus, the task management component 606 can update chores for all members of the family and/or employees in the home (e.g. maids, cooks, cleaners, gardeners, etc.) by synchronizing information between devices connected to the multiple femto APs within the enterprise. Further, the calendars of the family members can also be synchronized by the task management component 606 for certain events. For example, if the mother enters information, for example, "Dinner with the Smith family—12/22/08—7 pm" in her calendar on her mobile phone connected to a femto AP within the house, the task management component 606 can identify the change in information and update the calendars of all other members of the family over the internal network. In another aspect, all events on the children's calendars can be transferred to the parent's calendars by the task management component 606, such that, the parents can keep track of the children's activities. It can be appreciated that the task management component 606 can update events or synchronize calendars when the two or more devices connect to the home femto enterprise. Thus, a reduced charge can be applied for the communication over the internal network.

In accordance with yet another example, when the enterprise femto architecture is utilized in an office, the task management component 606 can be employed to synchronize calendars and/or contacts of different employees based in part on a policy 608, schedule 610, user preference 612 and/or white/black lists 614. As an example, a schedule for a board of directors meeting can be sent to the cellular phones of each member of the board of directors, which can be connected to disparate femto APs in the femto enterprise. Additionally, the task management component 606 can instruct the routing platform (102 in FIG. 2) to direct a meeting agenda, memo, minutes of meeting to specific employees in the office. The routing platform can accordingly direct the communication internally and reduce the traffic on the backhaul pipe. It can be appreciated that the subject specification is not limited to the above examples and the system 600 can be employed in different scenarios.

Figure 7:
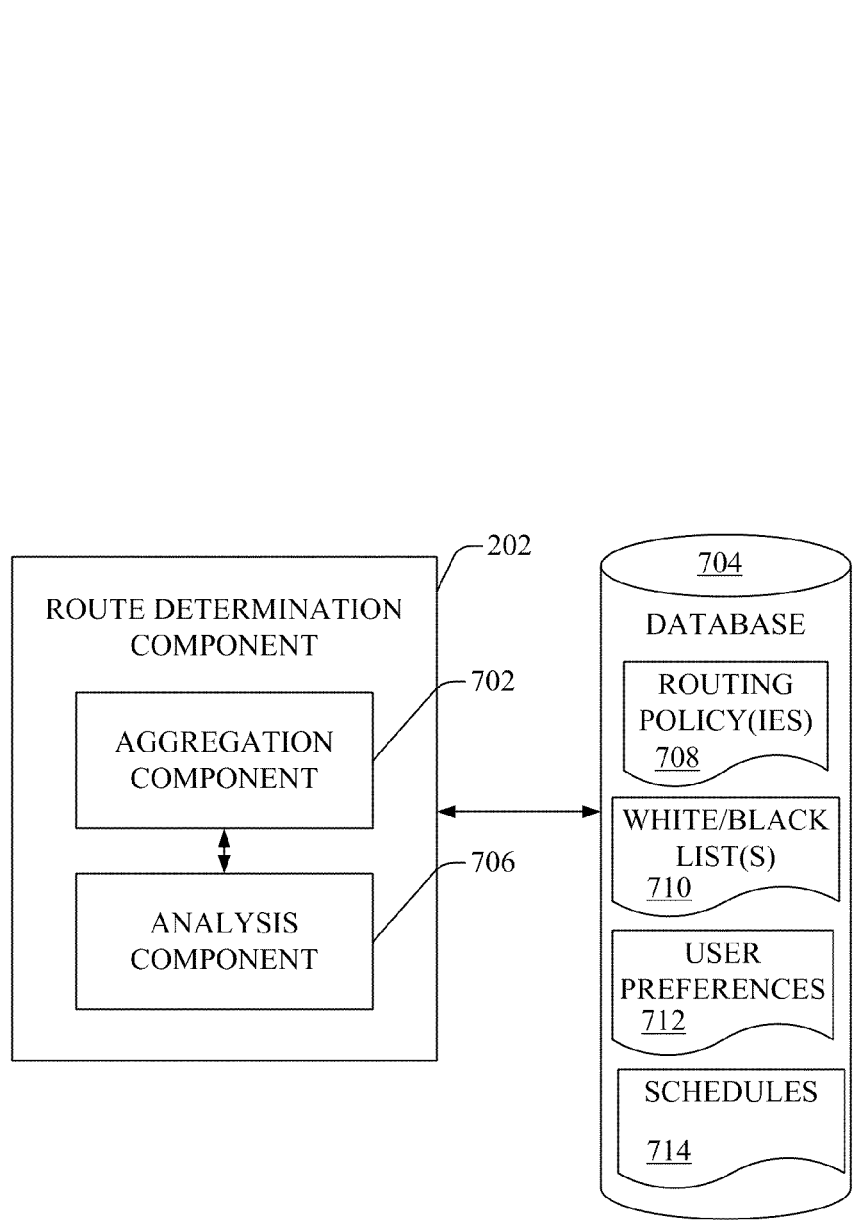
FIG. 7 illustrates an example system that can be employed to determine routing information for communication packets in an enterprise femto architecture, according to an aspect of the subject disclosure.

FIG. 7 illustrates an example system 700 that can be employed to determine routing information for communication packets in an enterprise femto architecture, according to an aspect of the subject disclosure. The route determination component 202 can typically manage tasks associated with routing packets received from femtos connected within the enterprise femto. It can be appreciated that the route determination component 202 can include functionality, as more fully described herein, for example, with regard to system 200.

According to an embodiment, the route determination component 202 can include an aggregation component 702 that receives registration data associated with the UEs attached to each femto connected to the routing platform in the femto enterprise network. Typically, the UEs can include most any electronic device that can connect wirelessly to the femto, such as, but not limited to, mobile phones, media players, digital cameras, media recorders, laptops, PDAs (personal digital assistants), personal computers, printers, scanners, digital photo frames, GPS module, gaming module, etc. Further, it can be appreciated the UEs can be mobile, stationary, and/or have limited mobility and can employed, for example, in a home, office, building, retail store, restaurant, hotel, factory, warehouse, etc.

The aggregation component 702 can aggregate the received registration information and store the aggregated data in a database, for example, database 704. According to an aspect, the aggregation component 702 can update the database 704 whenever a change in registration is detected. For example, a new UE connects to a femto, a registered UE disconnects from the femto, etc. It can be appreciated that the database 704 (and 604 in FIG. 6) described herein can include either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable PROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory of the subject systems and methods is intended to comprise, without being limited to, these and any other suitable types of memory. It can be appreciated that the description of database 704 above refers to internal and/or external memory such as, but not limited to, various types of media that are readable by a computer, such as zip drives, magnetic cassettes, flash memory cards, cartridges, and the like.

Typically, the route determination component 202 can include an analysis component 706 that evaluates a communication packet received by a routing platform from a femto. As an example, the packets can include data, voice, and/or media communication. Moreover, the analysis component 706 is employed to determine a route for the received packet based in part of an analysis of the packet. According to one aspect, analysis can be device based, message based, policy based, and/or a combination thereof. Specifically, device based analysis can determine a route for the packet based on identifier numbers, codes, or token of the UE, type of UE, resources available on the UE, services that can be utilized by the UE, type of technologies (e.g., communication technologies) supported by the UE, bandwidth requirements of the UE, bandwidth allocated to the UE, QoS policy associated with the UE etc. Further, message based analysis can include analysis of content in the message, size of the message, type or format of the message, flags in the message, etc.

As an example, the analysis component 706 can check a header associated with the received packet and determine a destination address. Based in part on the determined destination address and the aggregated registration information stored in the database 704, the analysis component 706 can determine whether the destination device is connected to the enterprise femto. In one aspect, routing can be determined by the analysis component based in part on flags or class associated with the SIM (subscriber identity module) in a UE.

Further, the analysis component 706 can employ policies 708, white/black list 710, user preferences 712, and/or schedules 714 stored in a database, for example, database 704 to determine a route for the received packet. In one aspect, a policy can be defined, for example, all data received from $UE_a$ from femto A can be internally routed to $UE_b$ on femto B. As an example, in a hospital scenario wherein an enterprise femto is employed, data received from machines associated with a particular patient connected to a femto AP can directly be routed to the mobile phone of a doctor in charge of the patient connected to a disparate femto AP within the femto enterprise.

Typically, white/black list 710 can also be employed by the analysis component 706 to facilitate routing. The white/black list 710 can store information regarding authorized devices that can be allowed to connect to a femto. In addition, the white/black list 710 can specify routing information associated with each authorized device. In an example, if packet is received from a UE on the white list, the analysis component 706 can determine that the packet can be internally transferred without utilizing the backhaul network. Similarly, if a black list is employed by the analysis component 706; all packets received from devices that are not on the black list can be routed internally, while the packets received from black listed devices can be routed to the core network. It can be appreciated that white/black lists can include source or destination UEs, and/or, content, size, type of message, etc. Further, the analysis component 706 can also employ user preferences 712 and/or schedules 714 to route the packet. Moreover, the user preferences 712 and/or schedules 714 can be specified by the wireless service provider, operator and/or end user.

According to an example, the analysis component 706 can determine an optimal route for a received packet, to avoid network congestion within the internal mesh network. Additionally or alternately, the analysis component 706 can employ load-balancing techniques to facilitate efficient network and/or resource utilization. The route determination component 202 can identify whether a packet received from a femto AP can be routed internally without accessing the core network by employing the analysis component 706. The determined route information can be sent to the routing platform by the route determination component. On receiving the determined route information, the routing platform (102 in FIG. 2) can direct the packet via the identified route.

Figure 8:
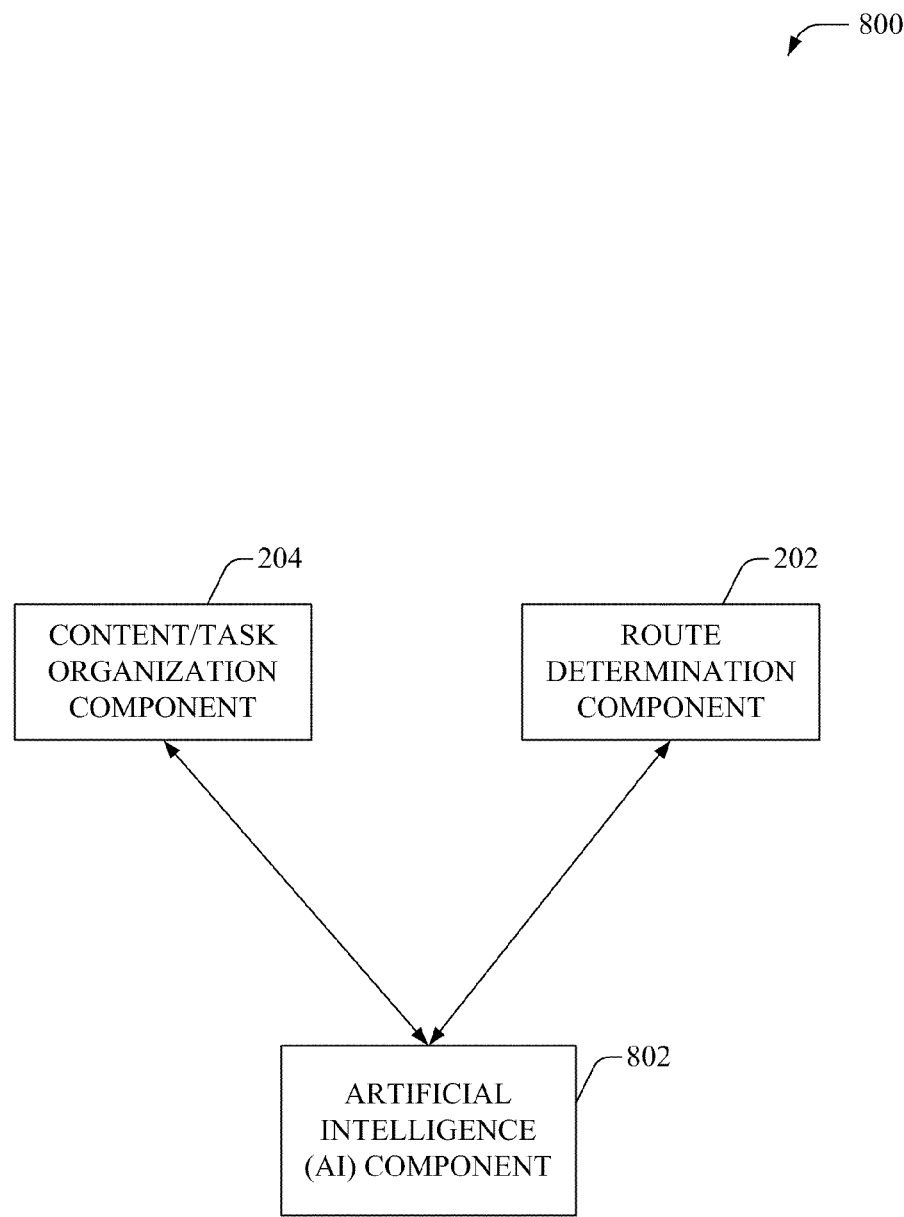
FIG. 8 illustrates an example system that employs machine learning techniques, which facilitates automating one or more features in accordance with the subject innovation

FIG. 8 illustrates a system 800 that employs an artificial intelligence (AI) component 802, which facilitates automating one or more features in accordance with the subject innovation. The subject innovation (e.g., in connection with route determination) can employ various AI-based schemes for carrying out various aspects thereof. For example, a process for determining how, when and where to route a packet received at the routing platform, or when and which calendars, contacts, tasks to synchronize in an enterprise femto architecture, can be facilitated via an automatic classifier system and process. Moreover, the classifier can be employed to determine a route that directs the packet from the routing platform to the destination. Further a classifier can also be employed to determine when and how to update a task list, contact list and/or calendar. A classifier is a function that maps an input attribute vector, x=(x1, x2, x3, x4, xn), to a confidence that the input belongs to a class, that is, f(x)= confidence(class). Such classification can employ a probabilistic and/or statistical-based analysis (e.g., factoring into the analysis utilities and costs) to prognose or infer an action that a user desires to be automatically performed. In the case of routing systems, for example, attributes can be flags, source, destination, etc or other data-specific attributes derived from the attributes, and the classes can be categories or areas of interest (e.g., levels of priorities).

A support vector machine (SVM) is an example of a classifier that can be employed. The SVM operates by finding a hypersurface in the space of possible inputs, which the hypersurface attempts to split the triggering criteria from the nontriggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria the devices that can be updated with information/content, the route for a received packet of communication, etc. The criteria can be based on the message, source or destination UE, source or destination femto AP, etc. As seen from FIG. 8, the AI component can facilitates automating one or more features of the content/task organization component 204 and/or the route determination component 202. It can be appreciated that the route determination component 202 and content/task organization component 204 can include functionality, as more fully described herein, for example, with regard to systems 200, 600 and 700.

Figure 9:
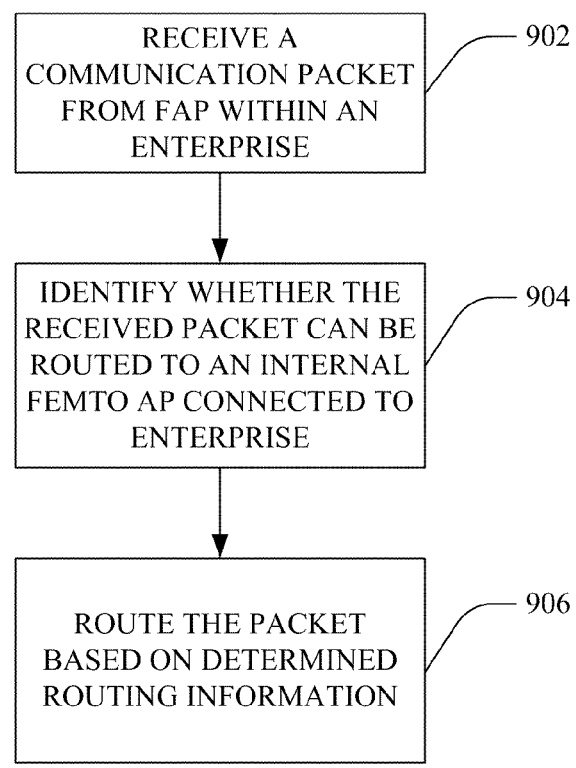
FIG. 9 illustrates an example methodology that that can be employed to efficiently manage bandwidth on a backhaul network in an enterprise femto architecture, according to an aspect of the subject innovation.
Figure 10:
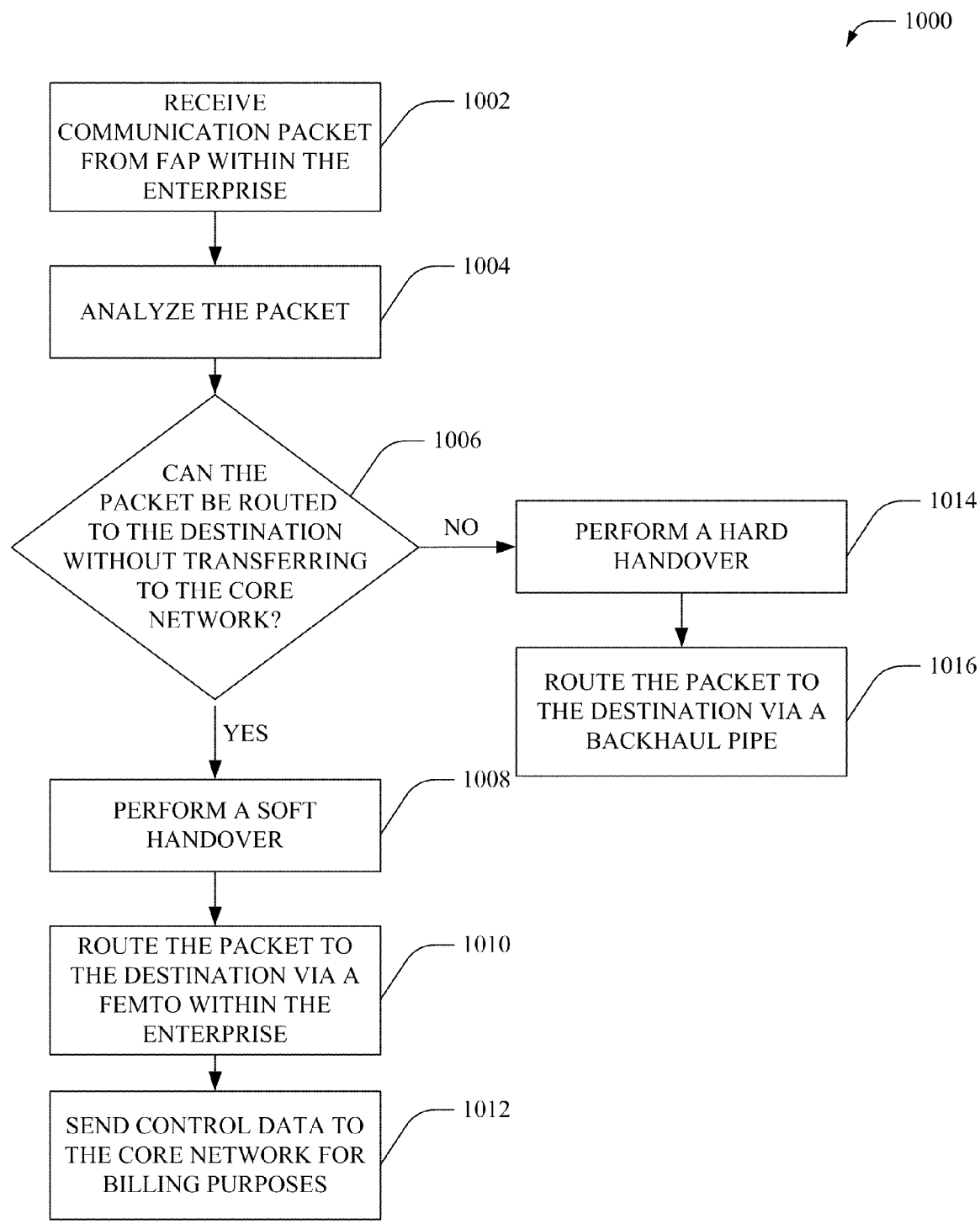
FIG. 10 illustrates example methodology that can be employed to facilitate communication routing in an enterprise femto architecture, according to an aspect of the subject innovation.
Figure 11:
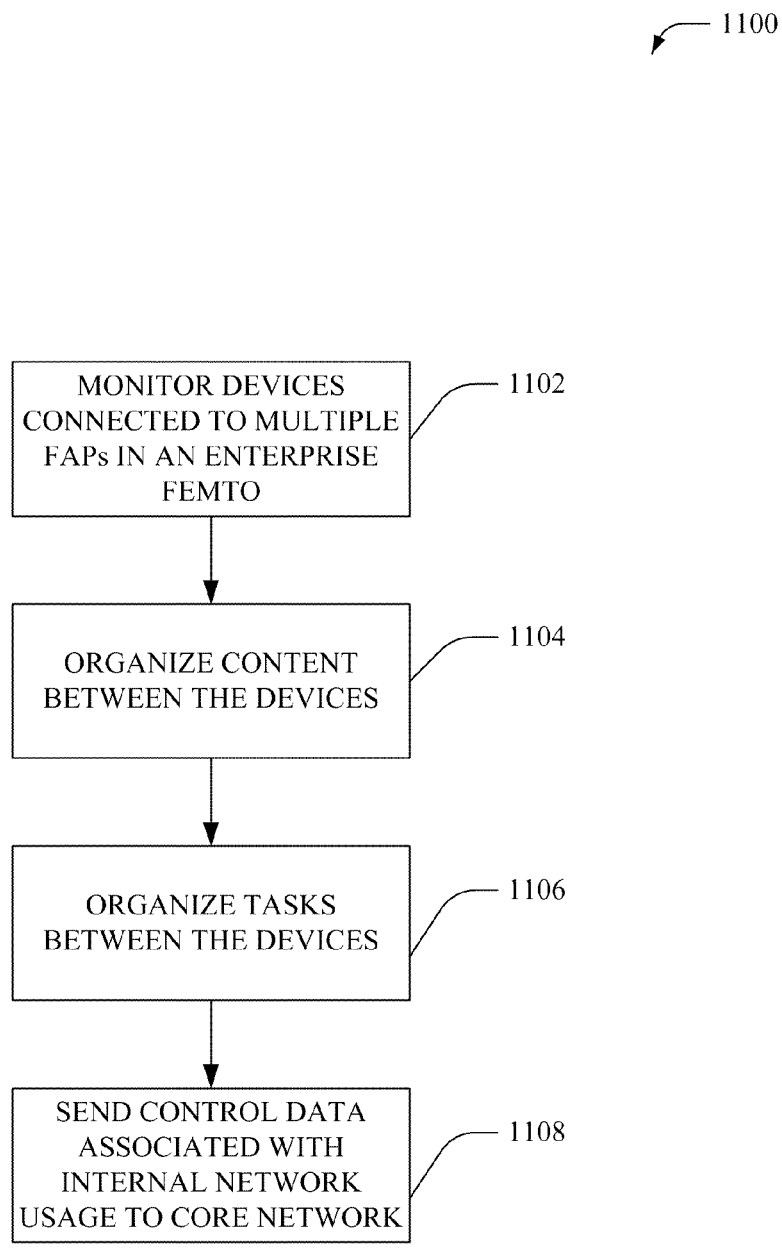
FIG. 11 illustrates an example methodology that can be employed to facilitate content/task management in an enterprise femto architecture in accordance with an aspect of the disclosure.

FIGS. 9-11 illustrate methodologies and/or flow diagrams in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

Referring now to FIG. 9, illustrated is an example methodology 900 that can be employed to efficiently manage bandwidth on a backhaul network in an enterprise femto architecture, according to an aspect of the subject innovation. Moreover, at 902, a communication packet can be received from one of the multiple femtos connected within the enterprise femto architecture. At 904, it can be identified whether the packet can be routed to a UE connected most any of the multiple femtos in the enterprise femto architecture based in part on an analysis of the packet and/or aggregated UE registration information. In one aspect, information associated with routing of the packet can be identified (e.g. source address, destination address, etc.). At 906, the packet can be routed based on routing information determined for transferring the packet.

In one example, the enterprise femto architecture can be employed in a factory. In particular, multiple femto APs can be deployed in the factory, such that, the coverage area of the femto APs can span the entire factory. Further, the multiple femto APs can be connected to a single backhaul pipe via a routing platform. An LTE based machine connected to a femto access point can send a communication packet (data, audio, video, etc.) to multiple mobile phones connected to various disparate femtos APs in the enterprise femto. The communication packet can be received and a determination can b e made whether the destination mobile phones are connected to femtos within the enterprise femto architecture based in part on an analysis of the packet and/or aggregated UE registration information. Accordingly, the packet can be directly routed to the multiple mobile phones without accessing the core network. In addition, control data associated with the communication can be saved and/or transferred to the core network. In another aspect, if determined that a destination mobile phone is not connected to any of the femto APs in the enterprise femto, then the packet can be routed to the core network via the backhaul network for delivery.

FIG. 10 illustrates an example methodology 1000 that can be employed to facilitate communication routing in an enterprise femto architecture, according to an aspect of the subject innovation. At 1002, a communication packet is received from a UE attached to a femto within the enterprise femto architecture. At 1004, received packet can be analyzed. In one aspect, the analysis can employ, information associated with the source UE, destination UE, message, priority, class, information from white/black lists, aggregated network information, policies, user preferences, etc. At 1006, a determination is made to identify if the packet can be internally routed to its destination without accessing the core network, based in part on the analysis. If determined that the packet can be internally routed, within the enterprise femto, a soft handover is performed at 1008, for example, between two or more femtos connected to routing platform. At 1010, the packet is routed to the destination UE via a femto within the femto enterprise. At 1012, control data associated with the packet transfer is sent to the core network, for example, via a femto gateway. The control data can be employed to facilitate billing for network usage. According to an aspect, if determined that the packet cannot be internally routed within the enterprise femto, a hard handover is performed at 1014. At, 1016, the packet is routed to its destination over the core network via a backhaul pipe.

Referring now to FIG. 11, there illustrated is an example methodology 1100 that can be employed to facilitate content/task management in an enterprise femto architecture in accordance with an aspect of the disclosure. According to an aspect, at 1102, devices attached to multiple femto access points (FAPs) can be monitored. At 1104, content can be organized between the devices, without accessing the core network. For example, content from a device attached to femto A, can be transferred to a device attached to femto B via a routing platform. At 1106, tasks can be organized between the devices, without accessing the core network. The content and task organization can include, but is not limited to, automatic synchronization of information in devices attached to different femtos in the enterprise network, such that core network is not accessed. For example, calendars, contacts lists, task lists, etc., can be synchronized, updated, and/or organized when a device attaches to a femto. As one example, content that is purchased and/or downloaded from the core network to the femto enterprise network can be accessed by or transferred internally, to most any device attached to a femto in the femto enterprise network, without the device requiring to purchase and/or download the content from the core network each time. At 1108, control information associated with the internal network usage, for example, during synchronization, can be sent to the core network to facilitate billing.

Figure 12A:
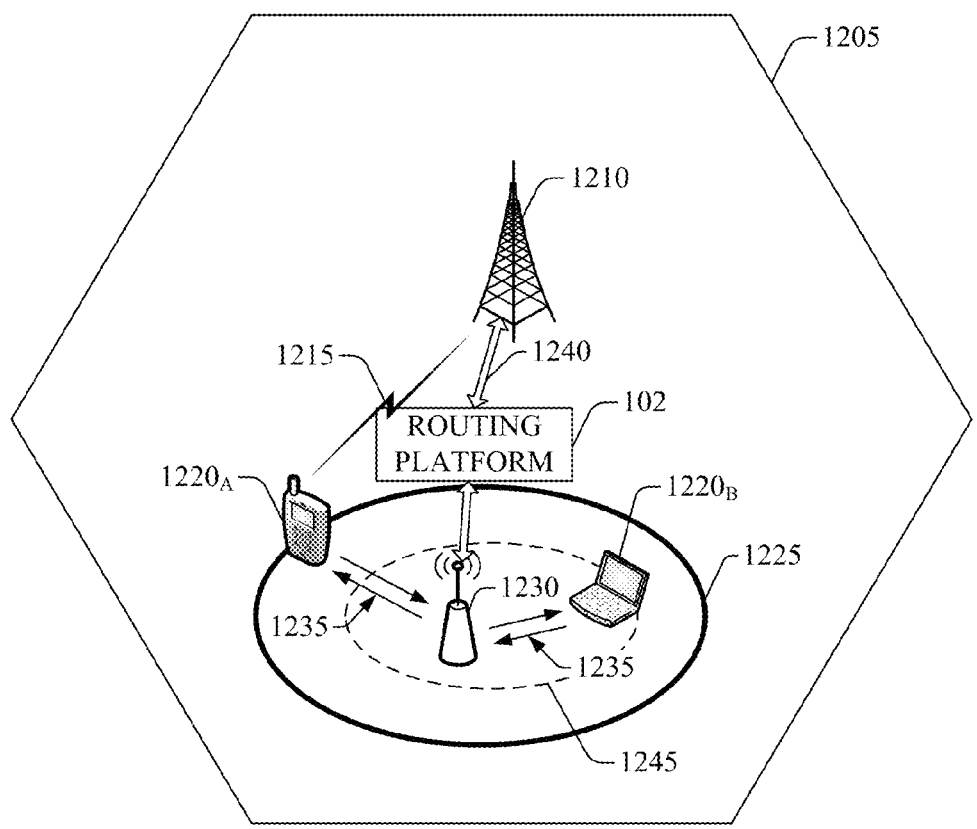
FIGS. 12A and 12B illustrate a schematic deployment of a macro cell and a femto cell for wireless coverage in accordance with aspects of the disclosure.

FIG. 12A illustrates a schematic wireless environment 1200 (e.g., a network) in which a femto cell can exploit various aspects of the subject innovation in accordance with the disclosed subject matter. In wireless environment 1200, area 1205 can represent a coverage macro cell, which can be served by base station 1210. Macro coverage is generally intended for outdoors locations for servicing mobile wireless devices, like UE 1220$_A$, and such coverage is achieved via a wireless link 1215. In an aspect, UE 1220 can be a 3GPP Universal Mobile Telecommunication System (UMTS) mobile phone.

Within macro coverage cell 1205, a femto cell 1245, served by a femto access point 1230, can be deployed. A femto cell typically can cover an area 1225 that is determined, at least in part, by transmission power allocated to femto AP 1230, path loss, shadowing, and so forth. Coverage area typically can be spanned by a coverage radius that ranges from 20 to 50 meters. Confined coverage area 1245 is generally associated with an indoors area, or a building, which can span about 5000 sq. ft. Generally, femto AP 1230 typically can service a number (e.g., a few or more) wireless devices (e.g., subscriber station 1220$_B$) within confined coverage area 1245. In an aspect, femto AP 1230 can integrate seamlessly with substantially any PS-based and CS-based network; for instance, femto AP 1230 can integrate into an existing 3GPP Core via conventional interfaces like Iu-CS, Iu-PS, Gi, Gn. In another aspect, femto AP 1230 can exploit high-speed downlink packet access in order to accomplish substantive bitrates. In yet another aspect, femto AP 1230 has a LAC (location area code) and RAC (routing area code) that can be different from the underlying macro network. These LAC and RAC are used to identify subscriber station location for a variety of reasons, most notably to direct incoming voice and data traffic to appropriate paging transmitters.

As a subscriber station, e.g., UE 1220$_A$, leaves macro coverage (e.g., cell 1205) and enters femto coverage (e.g., area 1225), as illustrated in environment 1200, UE 1220$_A$ can attempt to attach to the femto AP 1230 through transmission and reception of attachment signaling, effected via a FL/RL 1235; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that UE 1220 can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 1230) therefore can be inclined to minimize unnecessary LAU/RAU signaling activity at substantially any opportunity to do so, and through substantially any available means. It is to be noted that substantially any mitigation of unnecessary attachment signaling/control can be advantageous for femto cell operation. Conversely, if not successful, UE 1220 generally can be commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE 1220 can be allowed on femto cell 1225 and incoming voice and data traffic can be paged and routed to the subscriber station through the femto AP 1230. It is to be noted also that data traffic is typically routed through a backhaul broadband wired network backbone 1240 (e.g., optical fiber backbone, twisted-pair line, T1/E1 phone line, DSL, or coaxial cable) via a routing platform 102. Typically, multiple femto APs can be connected to the routing platform. Specifically, the routing platform can direct traffic internally to other femto APs if determined that the destination UE is connected to the other femto AP.

It is to be noted that as a femto AP 1230 generally can rely on a backhaul network backbone 1240 for routing and paging, and for packet communication, substantially any quality of service can handle heterogeneous packetized traffic. According to an aspect, the femto AP 1230 can connect to the backhaul network backbone 1240 via a routing platform that can facilitate efficient network usage of the backhaul network. Namely, packet flows established for wireless communication devices (e.g., terminals 1220$_A$ and 1220$_B$) served by femto AP 1230, and for devices served through the backhaul network pipe 1240. It is to be noted that to ensure a positive subscriber experience, or perception, it is desirable for femto AP 1230 to maintain a high level of throughput for traffic (e.g., voice and data) utilized on a mobile device for one or more subscribers while in the presence of external, additional packetized, or broadband, traffic associated with applications (e.g., web browsing, data transfer (e.g., content upload), and the like) executed in devices within the femto coverage area (e.g., area 1225 or area 1245).

Figure 12B:
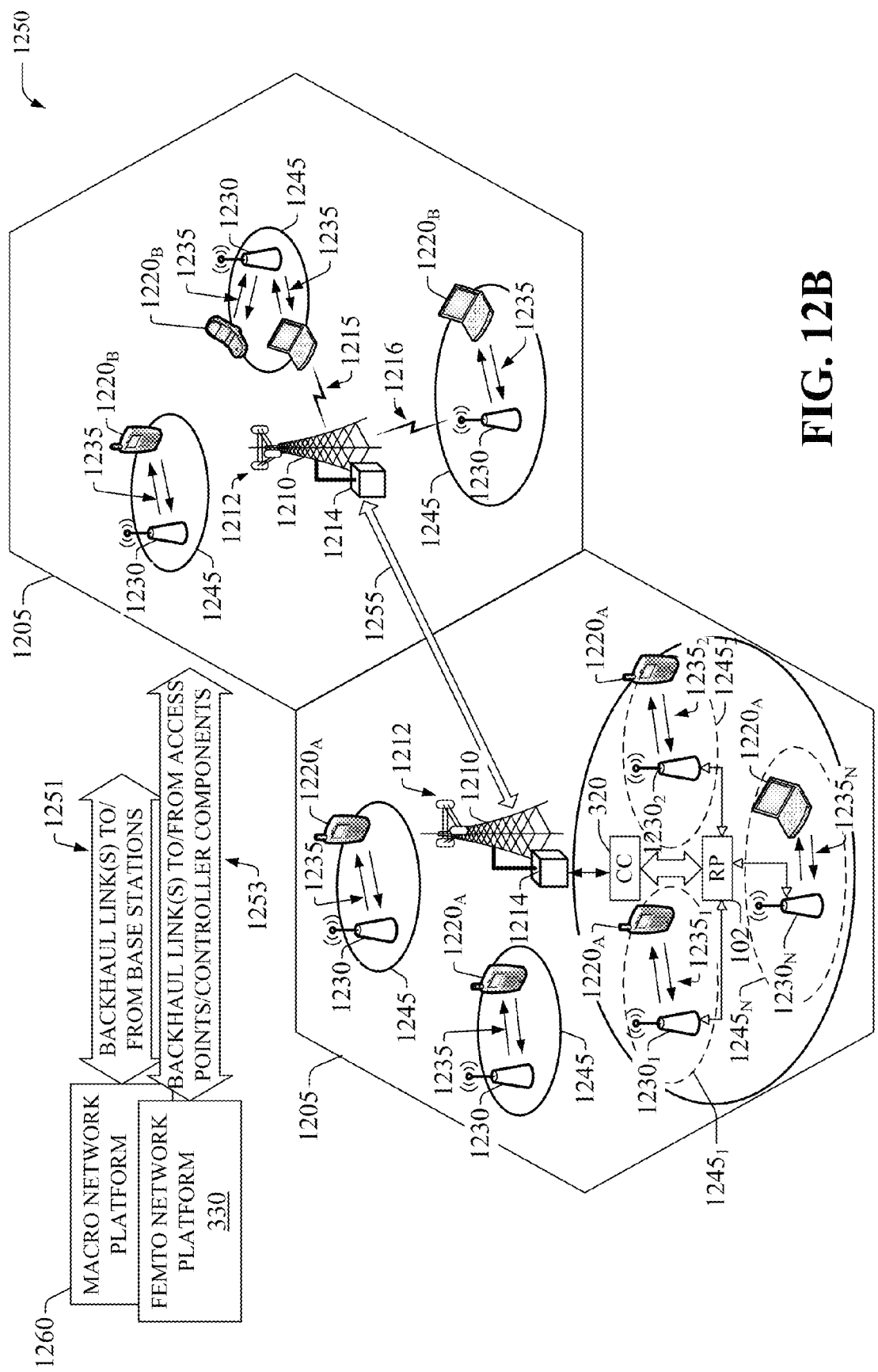

Referring to the drawings, FIG. 12B illustrates a wireless environment that includes macro cells and femtocells for wireless coverage in accordance with aspects described herein. In wireless environment 1250, two areas 1205 represent "macro" cell coverage, each macro cell is served by a base station 1210. It can be appreciated that macro cell coverage area 1205 and base station 1210 can include functionality, as more fully described herein, for example, with regard to system 1200. Macro coverage is generally intended to serve mobile wireless devices, like UE 1220$_A$, 1220$_B$, in outdoors locations. An over-the-air wireless link 115 provides such coverage, the wireless link 115 comprises a downlink (DL) and an uplink (UL), and utilizes a predetermined band, licensed or unlicensed, of the radio frequency (RF) spectrum. As an example, UE 1220$_A$, 1220$_B$ can be a 3GPP Universal Mobile Telecommunication System (UMTS) mobile phone. It is noted that a set of base stations, its associated electronics, circuitry or components, base stations control component(s), and wireless links operated in accordance to respective base stations in the set of base stations form a radio access network (RAN). In addition, base station 1210 communicates via backhaul link(s) 1251 with a macro network platform 1260, which in cellular wireless technologies (e.g., 3rd Generation Partnership Project (3GPP) Universal Mobile Telecommunication System (UMTS), Global System for Mobile Communication (GSM)) represents a core network.

In an aspect, macro network platform 1260 controls a set of base stations 1210 that serve either respective cells or a number of sectors within such cells. Base station 1210 comprises radio equipment 1214 for operation in one or more radio technologies, and a set of antennas 1212 (e.g., smart antennas, microwave antennas, satellite dish(es) . . . ) that can serve one or more sectors within a macro cell 1205. It is noted that a set of radio network control node(s), which can be a part of macro network platform; a set of base stations (e.g., Node B 1210) that serve a set of macro cells 1205; electronics, circuitry or components associated with the base stations in the set of base stations; a set of respective OTA wireless links (e.g., links 1215 or 1216) operated in accordance to a radio technology through the base stations; and backhaul link(s) 1255 and 1251 form a macro radio access network (RAN). Macro network platform 1260 also communicates with other base stations (not shown) that serve other cells (not shown). Backhaul link(s) 1251 or 1253 can include a wired backbone link (e.g., optical fiber backbone, twisted-pair line, T1/E1 phone line, a digital subscriber line (DSL) either synchronous or asynchronous, an asymmetric ADSL, or a coaxial cable . . . ) or a wireless (e.g., line-of-sight (LOS) or non-LOS) backbone link. Backhaul pipe(s) 1255 link disparate base stations 1210. According to an aspect, backhaul link 1253 can connect multiple femto access points 1230 and/or controller components (CC) 320 to the femto network platform 330. In one example, multiple femto APs can be connected to a routing platform (RP) 102, which in turn can be connect to a controller component (CC) 320. Typically, the information from UEs 1220$_A$ can be routed by the RP 102, for example, internally, to another UE 1220$_A$ connected to a disparate femto AP connected to the RP 102, or, externally, to the femto network platform 330 via the CC 302, as discussed in detail supra.

In wireless environment 1250, within one or more macro cell(s) 1205, a set of femtocells 1245 served by respective femto access points (APs) 1230 can be deployed. It can be appreciated that, aspects of the subject innovation are geared to femtocell deployments with substantive femto AP density, e.g., $10^4$-$10^7$ femto APs 1230 per base station 1210. According to an aspect, a set of femto access points 1230$_1$-1230$_N$, with N a natural number, can be functionally connected to a routing platform 102, which can be functionally coupled to a controller component 320. The controller component 320 can be operationally linked to the femto network platform 330 by employing backhaul link(s) 1253. Accordingly, UEs UE 1220$_A$ connected to femto APs 1230$_1$-1230$_N$ can communicate internally within the femto enterprise via the RP 102 and/or can also communicate with the femto network platform 330 via the RP 102, controller 320 and the backhaul link(s) 1253. It can be appreciated that although only one femto enterprise is depicted in FIG. 12B, multiple femto enterprise networks can be deployed within a macro cell 1205.

Figure 13:
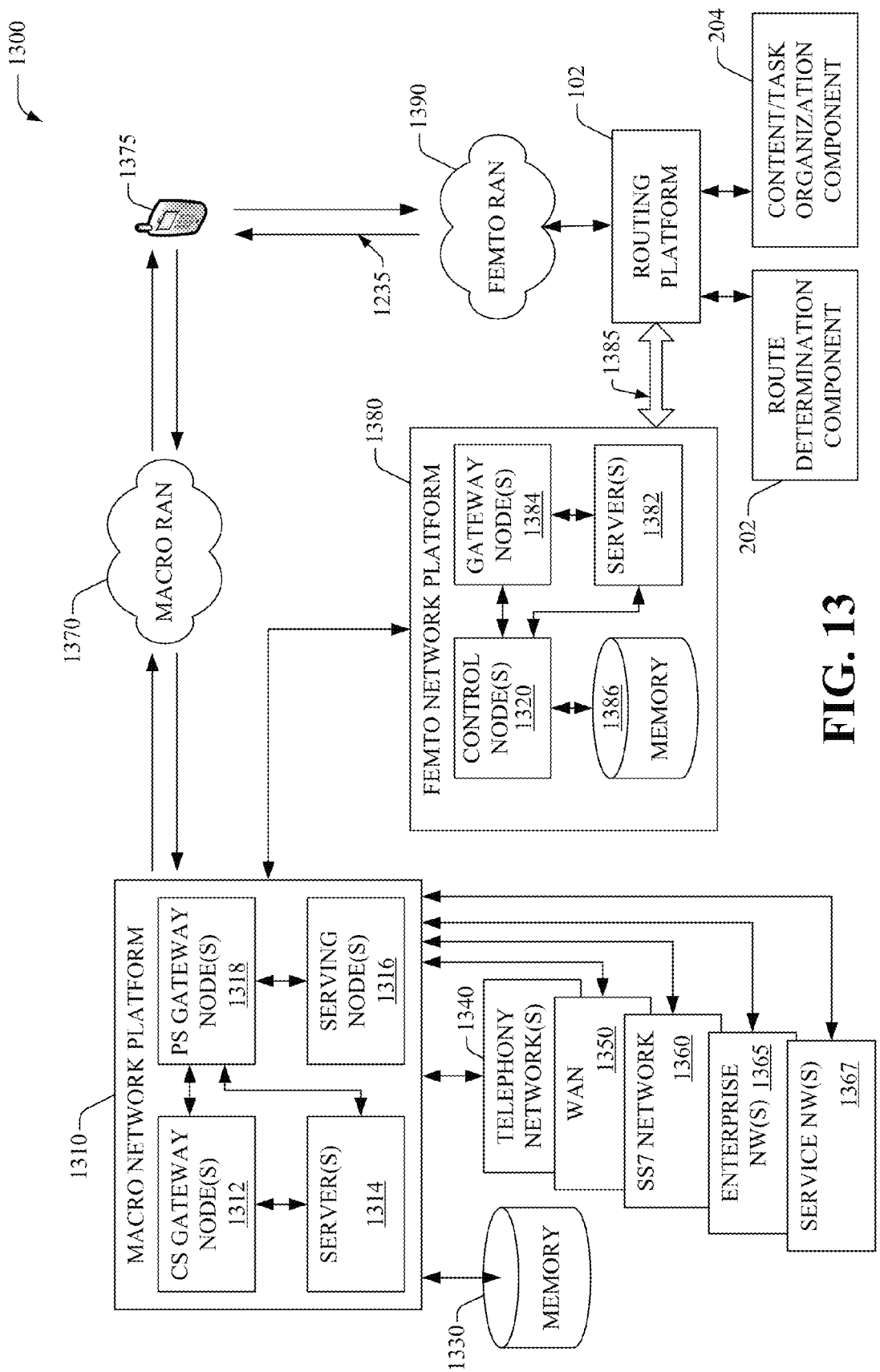
FIG. 13 illustrates an example wireless communication environment with associated components for operation of a femto cell in accordance with the subject specification.
Figure 14:
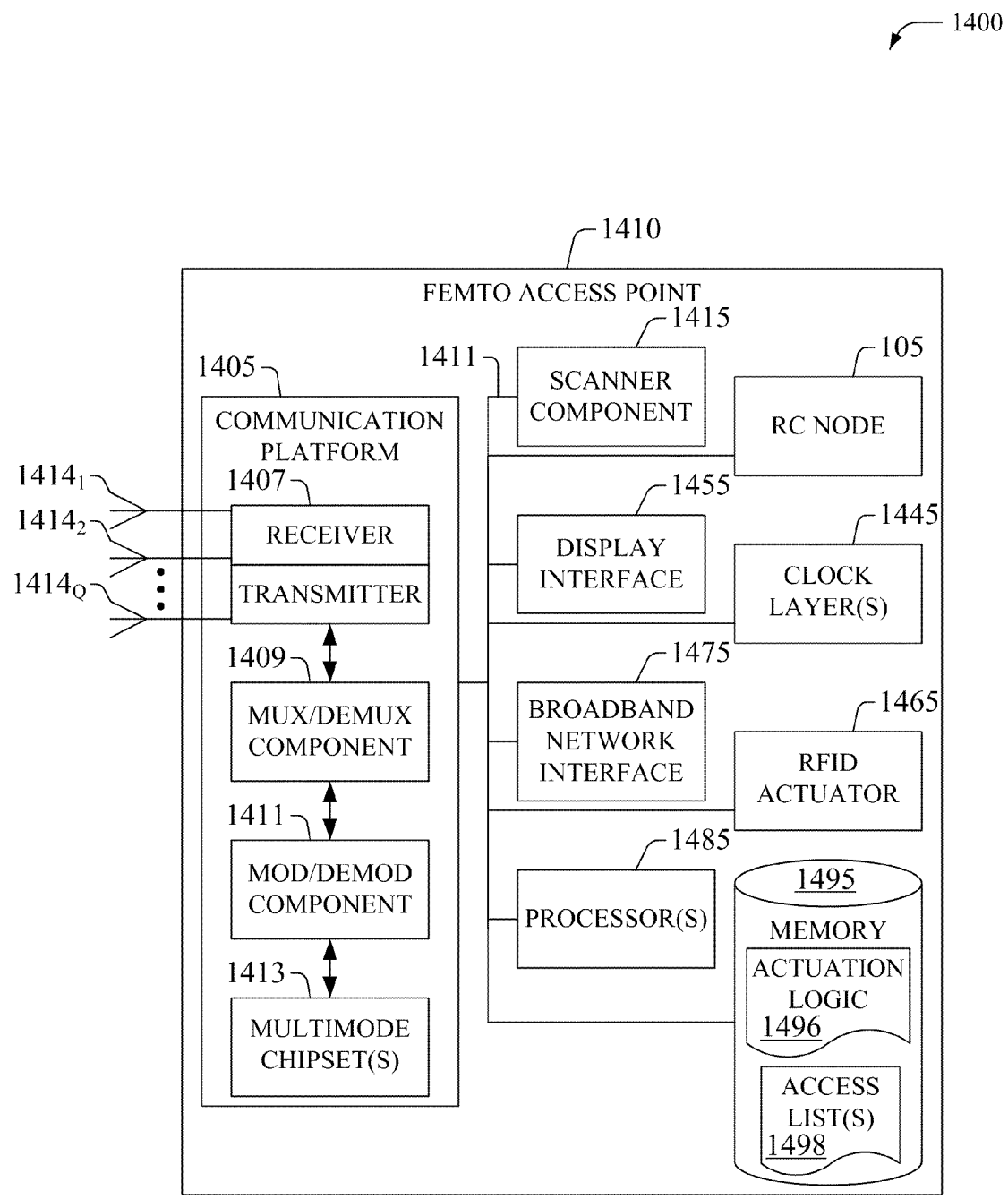
FIG. 14 illustrates an example embodiment of a femto access point that operates in accordance with aspects disclosed in the subject specification.

To provide further context for various aspects of the subject specification, FIGS. 13 and 14 illustrate, respectively, an example wireless communication environment 1300, with associated components for operation of a femto cell, and a block diagram of an example embodiment 1400 of a femto access point that can operate in accordance with aspects described herein.

Wireless communication environment 1300 includes two wireless network platforms: (i) A macro network platform 1310 that serves, or facilitates communication) with user equipment 1375 via a macro radio access network (RAN) 1370. It should be appreciated that in cellular wireless technologies (e.g., 4G, 3GPP UMTS, HSPA, 3GPP LTE, 3GPP UMB), macro network platform 1310 is embodied in a Core Network. (ii) A femto network platform 1380, which can provide communication with UE 1375 through a femto RAN 1390, linked to the femto network platform 1380 through a routing platform 102 via backhaul pipe(s) 1385, wherein backhaul pipe(s) are substantially the same a backhaul link 1240. It should be appreciated that femto network platform 1380 typically offloads UE 1375 from macro network, once UE 1375 attaches (e.g., through macro-to-femto handover, or via a scan of channel resources in idle mode) to femto RAN. Further, it can be appreciated that the routing platform 102 and context/task organization component 202 can include functionality, as more fully described herein, for example, with regard to systems 100, 200 and 600.

It is noted that RAN includes base station(s), or access point(s), and its associated electronic circuitry and deployment site(s), in addition to a wireless radio link operated in accordance with the base station(s). Accordingly, macro RAN 1370 can comprise various coverage cells like cell 1205, while femto RAN 1390 can comprise multiple femto access points. As mentioned above, it is to be appreciated that deployment density in femto RAN 1390 is substantially higher than in macro RAN 1370.

Generally, both macro and femto network platforms 1310 and 1380 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject innovation, macro network platform 1310 includes CS gateway node(s) 1312 which can interface CS traffic received from legacy networks like telephony network(s) 1340 (e.g., public switched telephone network (PSTN), or public land mobile network (PLMN)) or a SS7 network 1360. Circuit switched gateway 1312 can authorize and authenticate traffic (e.g., voice) arising from such networks. Additionally, CS gateway 1312 can access mobility, or roaming, data generated through SS7 network 1360; for instance, mobility data stored in a VLR, which can reside in memory 1330. Moreover, CS gateway node(s) 1312 interfaces CS-based traffic and signaling and gateway node(s) 1318. As an example, in a 3GPP UMTS network, gateway node(s) 1318 can be embodied in gateway GPRS support node(s) (GGSN).

In addition to receiving and processing CS-switched traffic and signaling, gateway node(s) 1318 can authorize and authenticate PS-based data sessions with served (e.g., through macro RAN) wireless devices. Data sessions can include traffic exchange with networks external to the macro network platform 1310, like wide area network(s) (WANs) 1350; it should be appreciated that local area network(s) (LANs) can also be interfaced with macro network platform 1310 through gateway node(s) 1318. Gateway node(s) 1318 generates packet data contexts when a data session is established. To that end, in an aspect, gateway node(s) 1318 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 1314. It is to be noted that in 3GPP UMTS network(s), gateway node(s) 1318 (e.g., GGSN) and tunnel interface (e.g., TTG) comprise a packet data gateway (PDG).

Macro network platform 1310 also includes serving node(s) 1316 that convey the various packetized flows of information or data streams, received through gateway node(s) 1318. As an example, in a 3GPP UMTS network, serving node(s) can be embodied in serving GPRS support node(s) (SGSN).

As indicated above, server(s) 1314 in macro network platform 1310 can execute numerous applications (e.g., location services, online gaming, wireless banking, wireless device management . . . ) that generate multiple disparate packetized data streams or flows, and manage (e.g., schedule, queue, format . . . ) such flows. Such application(s), for example can include add-on features to standard services provided by macro network platform 1310. Data streams can be conveyed to gateway node(s) 1318 for authorization/authentication and initiation of a data session, and to serving node(s) 1316 for communication thereafter. Server(s) 1314 can also effect security (e.g., implement one or more firewalls) of macro network platform 1310 to ensure network's operation and data integrity in addition to authorization and authentication procedures that CS gateway node(s) 1312 and gateway node(s) 1318 can enact. Moreover, server(s) 1314 can provision services from external network(s), e.g., WAN 1350, or Global Positioning System (GPS) network(s) (not shown). It is to be noted that server(s) 1314 can include one or more processor configured to confer at least in part the functionality of macro network platform 1310. To that end, the one or more processor can execute code instructions stored in memory 1330, for example.

In example wireless environment 1300, memory 1330 stores information related to operation of macro network platform 1310. Information can include business data associated with subscribers; market plans and strategies, e.g., promotional campaigns, business partnerships; operational data for mobile devices served through macro network platform; service and privacy policies; end-user service logs for law enforcement; and so forth. Memory 1330 can also store information from at least one of telephony network(s) 1340, WAN(s) 1350, or SS7 network 1360, enterprise NW(s) 1365, or service NW(s) 1367.

Femto gateway node(s) 1384 have substantially the same functionality as PS gateway node(s) 1318. Additionally, femto gateway node(s) 1384 can also include substantially all functionality of serving node(s) 1316. In an aspect, femto gateway node(s) 1384 facilitates handover resolution, e.g., assessment and execution. Further, control node(s) 1320 can receive handover requests and relay them to a handover component (not shown) via gateway node(s) 1384. According to an aspect, control node(s) 1320 can support RNC capabilities and can be substantially similar to the control component 320 (FIG. 3) and can include functionality thereof.

Server(s) 1382 have substantially the same functionality as described in connection with server(s) 1314. In an aspect, server(s) 1382 can execute multiple application(s) that provide service (e.g., voice and data) to wireless devices served through femto RAN 1390. Server(s) 1382 can also provide security features to femto network platform. In addition, server(s) 1382 can manage (e.g., schedule, queue, format . . . ) substantially all packetized flows (e.g., IP-based, frame relay-based, ATM-based) it generates in addition to data received from macro network platform 1310. It is to be noted that server(s) 1382 can include one or more processor configured to confer at least in part the functionality of macro network platform 1310. To that end, the one or more processor can execute code instructions stored in memory 1386, for example.

Memory 1386 can include information relevant to operation of the various components of femto network platform 1380. For example operational information that can be stored in memory 1386 can comprise, but is not limited to, subscriber information; contracted services; maintenance and service records; femto cell configuration (e.g., devices served through femto RAN 1390; access control lists, or white lists); service policies and specifications; privacy policies; add-on features; and so forth.

It is noted that femto network platform 1380 and macro network platform 1310 can be functionally connected through one or more reference link(s) or reference interface(s). In addition, femto network platform 1380 can be functionally coupled directly (not illustrated) to one or more of external network(s) 1340, 1350, 1360, 1365 or 1367. Reference link(s) or interface(s) can functionally link at least one of gateway node(s) 1384 or server(s) 1682 to the one or more external networks 1340, 1350, 1360, 1365 or 1367.

With respect to FIG. 14, in example embodiment 1400, femto cell AP 1410 can receive and transmit signal(s) (e.g., traffic and control signals) from and to wireless devices, access terminals, wireless ports and routers, etc., through a set of antennas $1414_1$-$1414_Q$. Femto AP 1410 can embody one or more of femtos 104 in FIG. 1, or femto APs $304_1$-$304_N$ in FIG. 3. The antennas $1414_1$-$1414_Q$ are part of communication platform 1405, which comprises electronic components and associated circuitry that provide for processing and manipulation of received signal(s) and signal(s) to be transmitted. The electronic components and circuitry can include a set of one or more chipsets, e.g., multimode chipset(s) 1413, that enable at least in part at least one of decoding, or deciphering, signal(s) conveyed to femto AP 1410 in various disparate radio technologies, or coding of signal(s) delivered from femto AP 1410 in accordance with various radio technology standards. In an aspect, communication platform 1405, via at least in part multimode chipset(s) 1413, can decode (i) GPS signaling such as timing messages generated, for example, by one or more deployed global navigation satellite systems (GNNSs) and relayed to femto AP 1410 through a routing platform, e.g., 110 in accordance with aspects described herein; or (ii) signal(s) received from a radio frequency identification (RFID) tag upon actuation thereof.

In an aspect, communication platform 1405 includes a receiver/transmitter 1407 that can convert signal from analog to digital upon reception, and from digital to analog upon transmission. In addition, receiver/transmitter 1407 can divide a single data stream into multiple, parallel data streams, or perform the reciprocal operation. Coupled to receiver/transmitter 1407 is a multiplexer/demultiplexer 1409 that facilitates manipulation of signal in time and frequency space. Electronic component 1409 can multiplex information (data or traffic and control or signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1409 can scramble and spread information (e.g., codes) according to substantially any code known in the art; e.g., Hadamard-Walsh codes, Baker codes, Kasami codes, polyphase codes, and so on. A modulator/demodulator component 1411 also is a part of communication platform 1405, and can modulate information according to multiple modulation techniques, such as frequency modulation, amplitude modulation (e.g., M-ary quadrature amplitude modulation (QAM), with M a positive integer), phase-shift keying (PSK), and the like. In an aspect, multimode chipset(s) 1413 can configure and enable mux/demux component 1409 and mod/demod component to operate in accordance with protocols or standards associated various radio technologies. Processor(s) 1485 also is functionally connected to communication platform 1405 and can enable operations on data (e.g., symbols, bits, or chips) for multiplexing/demultiplexing, such as effecting direct and inverse fast Fourier transforms or Hadamard transforms; or modulation/demodulation of data streams.

Femto access point 1410 also includes RC node 305, which can allocate radio resources, e.g., resource blocks, to a mobile device served through femto AP 1410, and schedule traffic among mobile devices, and device with wireless capability, served via femto AP 1410. In an aspect, RC node 305 can schedule traffic in accordance with at least one of semi-persistent scheduling, round robin, or proportional fair scheduling. Consistent with allocated radio resources, RC node 305 can select format(s) of data packet(s) and management packet(s) for traffic and signaling exchange amongst femto AP 1410 and a served mobile device. In addition, RC node 305 can select a radio technology and modulation formats and coding schemes compatible therewith. In an aspect, RC node 305 can configure operation of femto AP 1410 in multiple-input multiple-output (MIMO) mode of operation. Moreover, RC node 305 can determine and configure transmit power for communication effected via femto AP 1410. Furthermore, RC node 305 can configure one or more of antennas $1414_1$-$1414_Q$ in order to attain directionality of EM radiation employed for communication, or to shape coverage area in the vicinity of femto AP 1410, which can mitigate of deadspots or weakly covered regions. Traffic and signaling can exchanged with a routing platform, e.g., 102, through RC node 305.

In embodiment 1400, scanner component 1415 can decode received wireless signals and thus determine at least an index that identifies a mobile device (e.g., $302_1$) attached to, or that attempts attachment to, femto AP 1410 can be extracted and access can be granted or denied based at least in part on access list(s) 1498. In addition, scanner component 1415 can decode wireless signal(s) received as part of time-of-flight (TOF) measurements that can be employed to estimate range of a mobile device or device with wireless capability from femto AP 1410. In an aspect, femto AP 1410 can receive signaling that configures clock layer(s) 1445 in order to conduct TOF measurements; configuration can include selection of a clock source (not shown) within clock layer(s) 1425. It is noted that clock layer(s) 1445 also can be configured to relay timing messages or timing information generated through an external clock. TOF measurements assess wireless signal propagation timing between a femto AP and an apparatus with wireless capability(ies); the TOF measurements can include at least one of round trip time (RTT) measurements, time or arrival (TOA) measurements, time difference of arrival (TDOA) measurements, angle of arrival (AOA) measurements, or the like.

It is noted that through at least in part communication platform 1405, and multimode chipset(s) 1413 therein, scanner component 1415 can survey wireless signal(s) within a set of EM frequency bands that can include all EM frequency bands licensed by the service provider (e.g., personal communication services (PCS), advanced wireless services (AWS), general wireless communications service (GWCS), and so forth), all unlicensed frequency bands currently available for telecommunication (e.g., the 2.4 GHz industrial, medical and scientific (IMS) band or one or more of the 5 GHz set of bands), and all EM frequency bands in operation and not licensed to the service provider. In addition, scanner component 1415 can survey wireless signal(s) over a configurable and upgradable set of radio technologies that includes one or more of the following Wi-Fi, BlueTooth, IS-95, WiMAX, 3GPP2 UMB, Enhanced GPRS, 3GPP UMTS, 3GPP LTE, HSPA, HSDPA, HSUPA, or LTE Advanced. Processor(s) 1485 can enable communication platform 1405 to switch amongst radio technologies (e.g., IS-95, WiMAX . . . ) in order to effect telecommunication and enable a scan in accordance with configured demodulation and demultiplexing protocols associated with a radio technology; instructions necessary for implementation of such protocols can reside in memory 1495. Such radio technology agility can afford to serve mobile devices, e.g., $302_1$ or $302_2$, in FIG. 3, that operate in disparate radio technologies, or collect pilot signal(s) modulated and coded in accordance to various technologies.

To conduct a scan, scanner component 1415 exploits at least in part communication platform 1405 and electronic components therein. In an aspect, scanner component(s) 1415 can configure transceiver 1407 to collect signal in a specific frequency carrier, e.g., frequency channel. Such configuration can allow determination of uplink (UL) carrier frequency, or channel number, associated with communication of mobile device(s) within the enterprise femto network and in the vicinity of femto AP 1410; and carrier frequency of downlink (DL) of disparate femto APs in the vicinity of femto AP 1410. RC node 305 can deliver information that identifies carrier frequencies extracted through scanning the wireless environment of femto AP 1410. Such carrier-frequency information is delivered to a routing platform, e.g., 102, which can aggregate it to form a carrier-frequency map of telecommunications within the coverage area of an enterprise femto network.

Scanner component 1415 also can gather data on uplink (UL) signal strength and quality associated with a served mobile device, e.g., $302_1$, to effect, at least in part, handover from femto AP 1410 to a disparate target femto AP. To at least that end, scanner component 1415 can gather UL sounding signal(s) and analyze such signal(s) to determine DL channel quality or strength; analysis can be enabled at least in part via processor(s) 1485. In an aspect, signal strength can be determined through received signal strength indicators (RSSIs) or received signal code power (RSCP), while quality can be assessed through metrics such as signal-to-noise ratio (SNR), signal-to-noise-and-interference ratio (SNIR), or energy per chip over total received power ($E_c/N_0$).

In addition, femto AP 1410 includes display interface 1455, which can render functions that control functionality of femto AP 1410 or reveal operational conditions thereof. In addition, display interface 1455 can include a screen to convey information to an end user. In an aspect, display interface 1455 can be embodied in a liquid crystal display (LCD), a plasma panel, a monolithic thin-film based electrochromic display, or the like. Moreover, display interface 1455 also can include a component (e.g., speaker(s)) that facilitates communication of aural indicia, which can be employed in connection with messages that convey operational instructions to an end user or consumer. Display interface 1455 also can enable data entry (e.g., through a linked keypad or via touch gestures), which can allow femto AP 1410 to receive external commands, such as restart operation, flush a memory or buffer, configure an access list, etc.

Broadband network interface 1475 enables connection of femto AP 1410 to a routing platform, as described herein, through broadband link(s) such as link(s) ($314_\lambda$), which can enable incoming and outgoing data and signaling flow. In an aspect, broadband network interface 1475 can include a port component with substantially the same or the same functional aspects or features as port component 515. Broadband network interface 1475 can be internal or external to femto AP 1410, and it can utilize display interface 1455 for at least one of end-user interaction or status information delivery. Processor(s) 1485 can configure at least in part operation of one or more port(s), e.g., switching voltages in a dry contact or assignment of a logical address such as an IP address to a port, that can reside within broadband network interface 1475. It is noted that RC node 305 can conduct at least part of the assignment of logical address(es) to a port within broadband network interface.

Femto AP 1410 also includes an RFID actuation component 1465, also termed herein RFID actuator 1465, which can convey through communication platform 1405 specific control packets within a pilot signal in order to stimulate an RFID tag and retrieve information therein by decoding RF packet(s) received from the RFID tag in response. Actuation protocol(s) and code sequence hypotheses for decoding information retained in an RFID tag can be included in actuation logic 1496 stored in memory 1495.

Memory 1495 can retain data structures, code instructions and program modules, or substantially any type of software or firmware; system or device information; code sequences hypotheses, and modulation and multiplexing hypotheses; spreading and pilot transmission; femto AP floor plan configuration; and so on. Additionally, memory 1495 can retain content(s) (e.g., multimedia files, subscriber-generated data); security credentials (e.g., passwords, encryption keys, digital certificates, biometric reference indicators like voice recordings, iris patterns, fingerprints); or the like.

Processor(s) 1485 is functionally connected, through bus 1411 to component(s), platform, interface(s), layer(s) and substantially any or any functional element that resides within femto AP 1410. Bus 1411 can be embodied in at least one of a memory bus, a system bus, an address bus, or one or more reference link(s) or interface(s). In an aspect, processor(s) 1485 is functionally coupled, e.g., via a memory bus within at least a portion of bus 1411, to memory 1495 in order to store therein and retrieve there from information to operate or confer functionality to the components, platform, interface(s), layer(s) and substantially any or any functional element that reside within femto AP 1410.

It is to be noted that aspects, features, or advantages of the subject innovation described in the subject specification can be exploited in substantially any wireless communication technology. For instance, 4G, Enhanced GPRS, 3GPP LTE, 3GPP2 UMB, 3GPP UMTS, HSPA, or Zigbee. Additionally, substantially all aspects of the subject innovation as disclosed in the subject specification can be exploited in legacy telecommunication technologies; e.g., GSM.

In addition, it is to be noted that the various aspects disclosed in the subject specification can also be implemented through (i) program modules stored in a computer-readable storage medium or memory (e.g., memory 1386 or memory 1455) and executed by a processor (e.g., processor 1445), or (ii) other combination(s) of hardware and software, or hardware and firmware.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," "data storage," "database," and substantially any other information storage component relevant to operation and functionality of a component, refer to "memory components," or entities embodied in a "memory" or components comprising the memory. It will be appreciated that the memory components, or computer-readable storage media, described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
a routing platform that connects multiple femto access points to a core mobility network via a common backhaul link, wherein the routing platform receives, from a first device coupled to a first femto access point of the multiple femto access points, a communication that is directed to a second device; and
a content organization component, within the routing platform, that directs the communication to the second device without transmission of at least a portion of data associated with the communication to the core mobility network via the common backhaul link, based on detecting that the second device is currently coupled to a second femto access point of the multiple femto access points.

2. The system of claim 1, further comprising: a route determination component that identifies routing information associated with the communication and transmits the routing information to the routing platform.

3. The system of claim 1, wherein the content organization component synchronizes data between the first and the second device without accessing the core mobility network.

4. The system of claim 3, wherein the content organization component employs a user preference to facilitate synchronization of the data.

5. The system of claim 1, further comprising: an aggregation component that receives registration data, associated with the second device, that is employed to determine a route for the communication.

6. The system of claim 1, further comprising: an analysis component that determines that the communication is to be routed internally, without accessing the core mobility network, based in part on an evaluation of the communication.

7. The system of claim 6, wherein the routing platform performs a soft handover and directs the communication to the second femto access point connected within the femto enterprise, in response to a determination by the analysis component that the communication is to be routed internally.

8. The system of claim 1, wherein the routing platform performs a hard handover and directs the communication to the core mobility network via the common backhaul link, in response to a determination that the second device is not currently coupled to one of the multiple femto access points.

9. The system of claim 7, wherein the at least the portion of data includes user plane data associated with the communication and wherein the routing platform transmits control plane data associated with the communication to the core mobility network, in response to the communication being routed internally.

10. A method, comprising:
connecting, by a system comprising at least one processor, multiple femto access points to a core mobility network via a common backhaul pipe to generate a femto enterprise mesh network;
receiving, by the system, a communication from a first user equipment coupled to a first femto access point of the multiple femto access points; and,
routing, by the system, at least a portion of data associated with the communication to a second user equipment, without transmission of at least the portion of the data to the core mobility network via the common backhaul pipe, based on determining that the second device is currently coupled to a second femto access point of the multiple femto access points.

11. The method of claim 10, further comprising: analyzing, by the system, the communication to facilitate the routing.

12. The method of claim 10, wherein the routing includes performing a soft handover to direct the at least a portion of data to the second femto access point.

13. The method of claim 12, wherein the routing includes routing user plane data associated with the communication to the second user equipment, without transmission of the user plane data to the core mobility network via the common backhaul pipe, and the method further comprises: transferring, by the system, control plane data associated with the communication to the core mobility network via the common backhaul pipe.

14. The method of claim 10, further comprising: synchronizing, by the system, data between the first user equipment and the second user equipment without transmitting the data via the accessing a core network, based in part on a user preference.

15. The method of claim 10, wherein the routing is based in part on information associated with an access control list associated with the multiple femto access points.

16. A non-transitory computer-readable storage medium having instructions stored thereon that, in response to execution, cause a system to perform operations, comprising:
connecting multiple femto access points to a core mobility network via a common backhaul pipe; and
routing at least a portion of data received from a first user equipment coupled to a first of the multiple femto access points, to a second user equipment coupled to a second of the multiple femto access points, without transmission of at least the portion of the data to the core mobility network via the common backhaul pipe and based on an analysis of the data.

17. The non-transitory computer-readable storage medium system of claim 16, wherein the operations further comprise: aggregating user equipment registration data received from the multiple femto access points, that identifies a set of user equipment currently connected to the multiple femto access points.

18. The non-transitory computer-readable storage medium system of claim 17, wherein the routing is based in part on an analysis of the aggregated user equipment registration data.

19. The non-transitory computer-readable storage medium system of claim 16, wherein the routing includes performing a soft handover to facilitate a transfer of user plane data to the second of the multiple femto access points, without transmission of the user plane data to the core mobility network via the common backhaul pipe and the operations further comprise transmitting control information associated with the transfer to the core mobility network to facilitate billing.

20. The non-transitory computer-readable storage medium system of claim 16, wherein the operations further comprise: synchronizing data between the first user equipment and the second user equipment without accessing the core mobility network, based in part on white list data associated with at least a portion of the multiple femto access points.

* * * * *